United States Patent
Tsao

(10) Patent No.: US 10,863,737 B2
(45) Date of Patent: Dec. 15, 2020

(54) CULTURE CONTAINER, AND SYSTEM AND METHOD OF TRANSFERRING A CULTURED ORGANISM BETWEEN CULTURE CONTAINERS

(71) Applicant: DROBOT BIOTECHNOLOGY LIMITED COMPANY, Taipei (TW)

(72) Inventor: Chia-Kang Tsao, Taiwan (TW)

(73) Assignee: DROBOT BIOTECHNOLOGY LIMITED COMPANY, Taipei (TW)

(*) Notice: Subject to any disclaimer, the term of this patent is extended or adjusted under 35 U.S.C. 154(b) by 668 days.

(21) Appl. No.: 15/692,520

(22) Filed: Aug. 31, 2017

(65) Prior Publication Data

US 2018/0332842 A1  Nov. 22, 2018

Related U.S. Application Data

(60) Provisional application No. 62/509,719, filed on May 22, 2017.

(51) Int. Cl.
*A01K 67/033* (2006.01)
*C12M 1/24* (2006.01)
*B65G 47/90* (2006.01)
*A01N 1/02* (2006.01)
*C12M 1/00* (2006.01)
(Continued)

(52) U.S. Cl.
CPC .......... *A01N 1/0263* (2013.01); *A01K 67/033* (2013.01); *A01N 1/0242* (2013.01); *C12M 21/00* (2013.01); *C12M 23/08* (2013.01); *C12M 23/24* (2013.01); *C12M 23/34* (2013.01);
(Continued)

(58) Field of Classification Search
CPC ...... B65G 47/52; B65G 47/90; A01K 67/033; A01K 1/031; A01K 29/005; A01K 1/0245; A01K 1/035; A01K 63/003; A01K 29/00; C12M 23/38; C12M 23/50; A01N 1/0263

USPC ............... 119/6.5, 421, 416, 417, 452, 496; 198/339.1

See application file for complete search history.

(56) References Cited

U.S. PATENT DOCUMENTS 2,151,589 A * 3/1939 Falls ...................... B65D 85/50
                                                            119/6.5
4,106,438 A 8/1978 Nelson
(Continued)

FOREIGN PATENT DOCUMENTS

| EP | 0339775 A2 | 2/1989 |
| GB | 1015519 | 1/1966 |
| WO | 2016134221 A1 | 8/2016 |

OTHER PUBLICATIONS

The Search Report from co-pending European Patent Application No. 18173221.5 dated Oct. 26, 2018.

*Primary Examiner* — Yvonne R Abbott-Lewis
(74) *Attorney, Agent, or Firm* — Baker & McKenize

(57) ABSTRACT

A culture container includes a tube having a first and a second opening respectively provided at two opposite ends thereof, and a cover attachable to and removable from the first opening of the tube, the cover including an inlet port for passage of a fluid substance and a receptacle for holding a substance consumable by an organism of interest, the receptacle being enclosed inside the tube and the inlet port communicating with a hollow interior of the tube when the cover is attached to the first opening of the tube. Moreover, a system and a method of transferring a cultured organism of interest include switching the covers between two culture containers.

17 Claims, 24 Drawing Sheets

(51) Int. Cl.
*C12M 1/04* (2006.01)
*C12M 1/26* (2006.01)
*C12M 1/36* (2006.01)

(52) U.S. Cl.
CPC ............ *C12M 23/38* (2013.01); *C12M 23/50* (2013.01); *C12M 33/04* (2013.01); *C12M 41/48* (2013.01)

(56) References Cited

U.S. PATENT DOCUMENTS

| | | | | |
|---|---|---|---|---|
| 4,212,267 | A | * | 7/1980 | Patterson ............... A01K 1/031 119/6.5 |
| 5,272,926 | A | * | 12/1993 | Wilkins ................. C12M 33/04 422/547 |
| 5,403,741 | A | * | 4/1995 | Holbrook ............... C12M 23/06 435/288.2 |
| 5,827,174 | A | | 10/1998 | Reuss, Jr. et al. |
| 5,902,745 | A | | 5/1999 | Butler et al. |
| 5,928,935 | A | | 7/1999 | Reuss, Jr. et al. |
| 6,223,687 | B1 | * | 5/2001 | Windle ............... A01K 67/0332 119/6.7 |
| 2013/0319334 | A1 | * | 12/2013 | Newton ................. A01K 29/00 119/6.5 |
| 2016/0066552 | A1 | * | 3/2016 | Arsiwalla ............ A01K 1/0047 119/6.5 |
| 2016/0075983 | A1 | | 3/2016 | He |
| 2016/0108351 | A1 | | 4/2016 | Lee |

\* cited by examiner

CULTURE CONTAINER, AND SYSTEM AND METHOD OF TRANSFERRING A CULTURED ORGANISM BETWEEN CULTURE CONTAINERS

CROSS-REFERENCE TO RELATED APPLICATION(S)

This application claims priority to U.S. Provisional Patent Application No. 62/509,719 filed on May 22, 2017, the disclosure of which is entirely incorporated herein by reference.

BACKGROUND

1. Field of the Invention

The present invention relates to culture containers, and systems and methods of transferring a cultured organism between culture containers.

2. Description of the Related Art

*Drosophila* species, such as *Drosophila melanogaster* (also known as fruit flies), have been extensively used in genetic research and is a common model organism in biology studies. Cultures of fruit flies are usually made in vials or bottles. For maintaining stocks of the fruit flies for a long period of time, the cultures of fruit flies have to be periodically transferred to new vials or bottles. This transfer process may be challenging to achieve for large-scale cultures involving thousands of stocks, wherein the cultured organism in each vial or bottle has to be transferred to a clean new vial or bottle without introducing contaminants that may alter the cultured stock.

Some existing equipment may use robot arms to facilitate the transfer process. For example, for transferring a culture of fruit flies from one vial to a new vial, the transfer process includes stunning the fruit flies, opening the two vials, using the robot arms to position the two vials so that their respective openings are in close contact with each other, and transferring the fruit flies from the current vial to the new vial. This approach may be time-consuming and require a sophisticated control, e.g., for properly positioning the vials so that the fruit flies can be transferred without introducing contaminants, or without fruit flies dropping outside the vials, which may contaminate subsequently processed vials.

Therefore, there is a need for a design that can achieve the transfer process in a more efficient manner, and address or improve at least the foregoing issues.

SUMMARY

The present application describes culture containers, and systems and methods of transferring a cultured organism between culture containers. A culture container described herein includes a tube having a first and a second opening respectively provided at two opposite ends thereof, and a cover attachable to and removable from the first opening of the tube, the cover including an inlet port for passage of a fluid substance and a receptacle for holding a substance consumable by an organism of interest, the receptacle being enclosed inside the tube and the inlet port communicating with a hollow interior of the tube when the cover is attached to the first opening of the tube.

A transfer system described herein includes a first conveyor system, a second conveyor system and an exchanging unit. The first conveyor system can transport at least a first culture container along a first path, wherein the first culture container includes a first tube having two openings at two opposite ends thereof and a removable first cover attached to one of the two openings of the first tube, the first cover including a first receptacle for holding a substance consumable by an organism of interest, the first receptacle being enclosed inside the first tube when the first cover is attached to the first tube. The second conveyor system can transport at least a second culture container along a second path, wherein the second culture container includes a second tube having two openings at two opposite ends thereof and a removable second cover attached to one of the two openings of the second tube, the second cover including a second receptacle for holding a substance consumable by an organism of interest, the second receptacle being enclosed inside the second tube when the second cover is attached to the second tube. The exchanging unit is disposed between the first and second conveyor systems, and is operable to interchange the first and second covers between the first and second culture containers so that the first cover is attached to the second tube and the second cover is attached to the first tube.

Moreover, the present application describes a method of transferring a cultured organism of interest through a transfer system. The method includes at least providing a first culture container enclosing an organism of interest, and providing a clean second culture container. The first culture container includes a first tube having two openings at two opposite ends thereof, a first cover closing one of the two openings of the first tube, and a first air-permeable plug closing the other one of the two openings of the first tube, the first cover including a first receptacle that is enclosed inside the first tube and holds a substance consumable by the organism and new generations of the organism. The second culture container includes a second tube having two openings at two opposite ends thereof, a second cover closing one of the two openings of the second tube, and a second air-permeable plug closing the other one of the two openings of the second tube, the second cover including a second receptacle that is enclosed inside the second tube and holds a substance consumable by the organism. In addition, the method further includes interchanging the first and second covers between the first and second culture containers so that the first cover is attached to the second tube and the second cover is attached to the first tube.

DETAILED DESCRIPTION OF THE EMBODIMENTS

Figure 1:
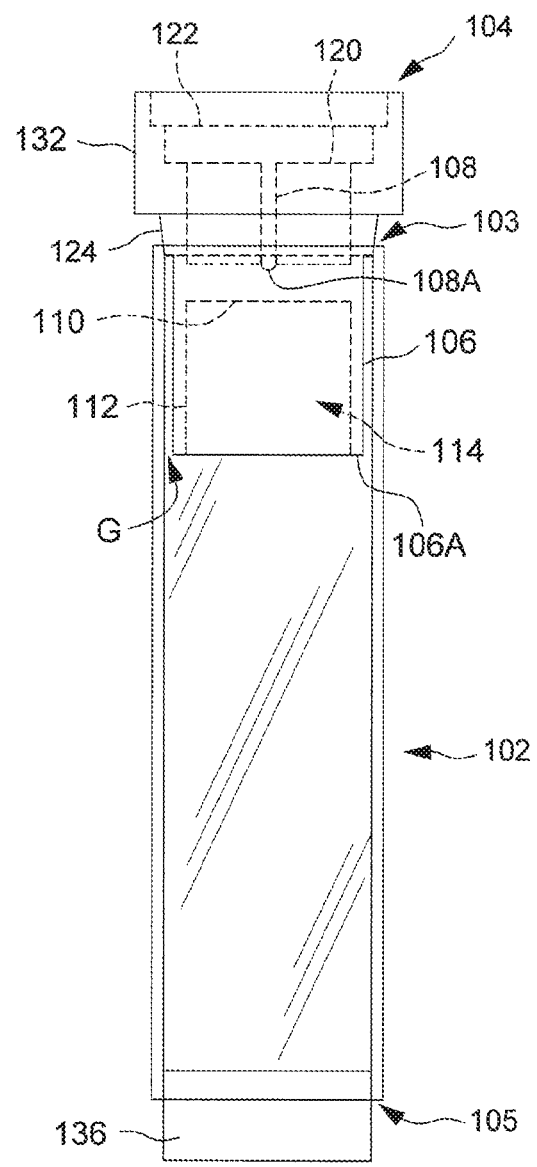
FIG. 1 is a perspective view illustrating an embodiment of a culture container.
Figure 2:
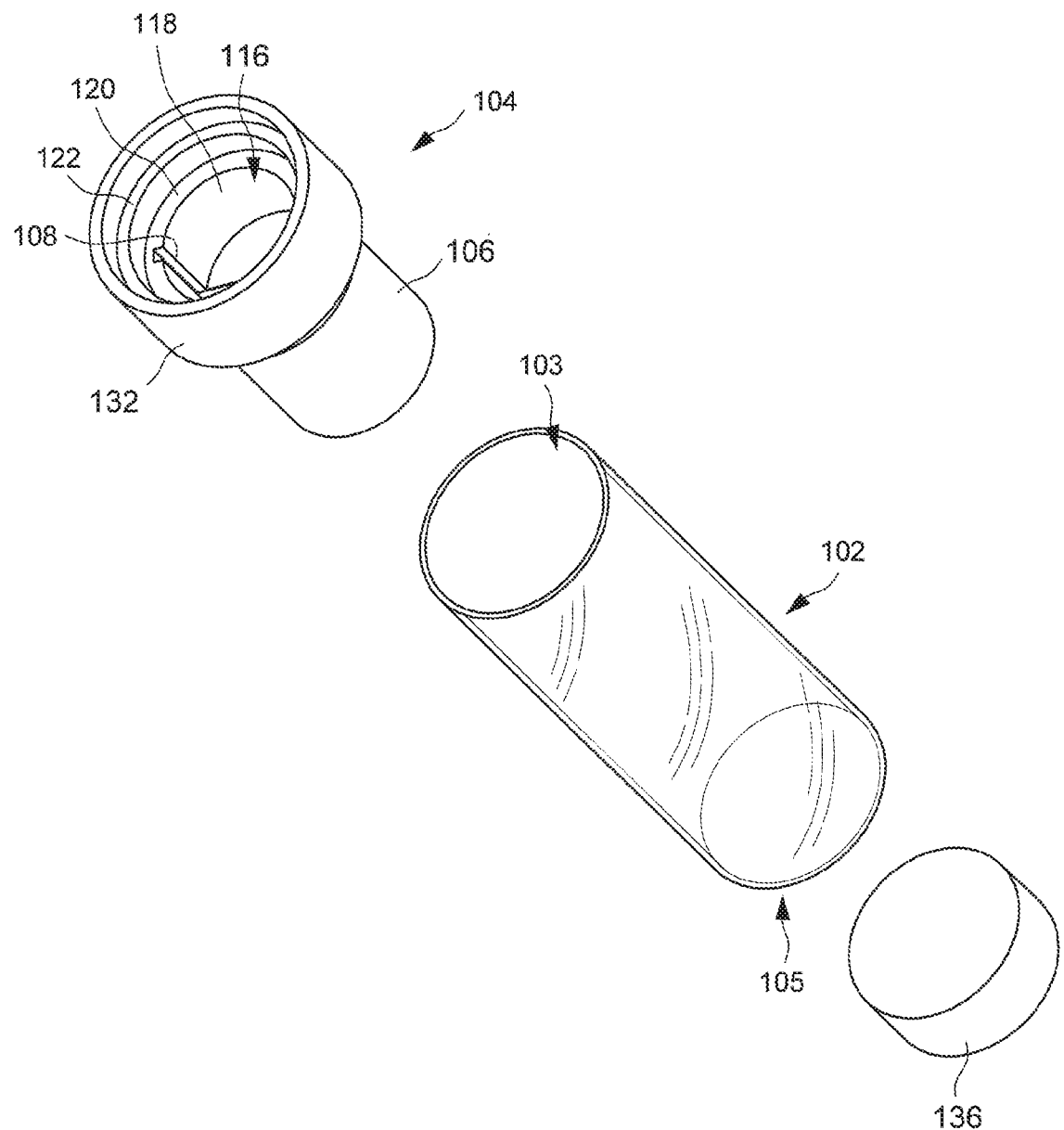
FIG. 2 is an exploded view of the culture container shown in FIG. 1.
Figure 3:
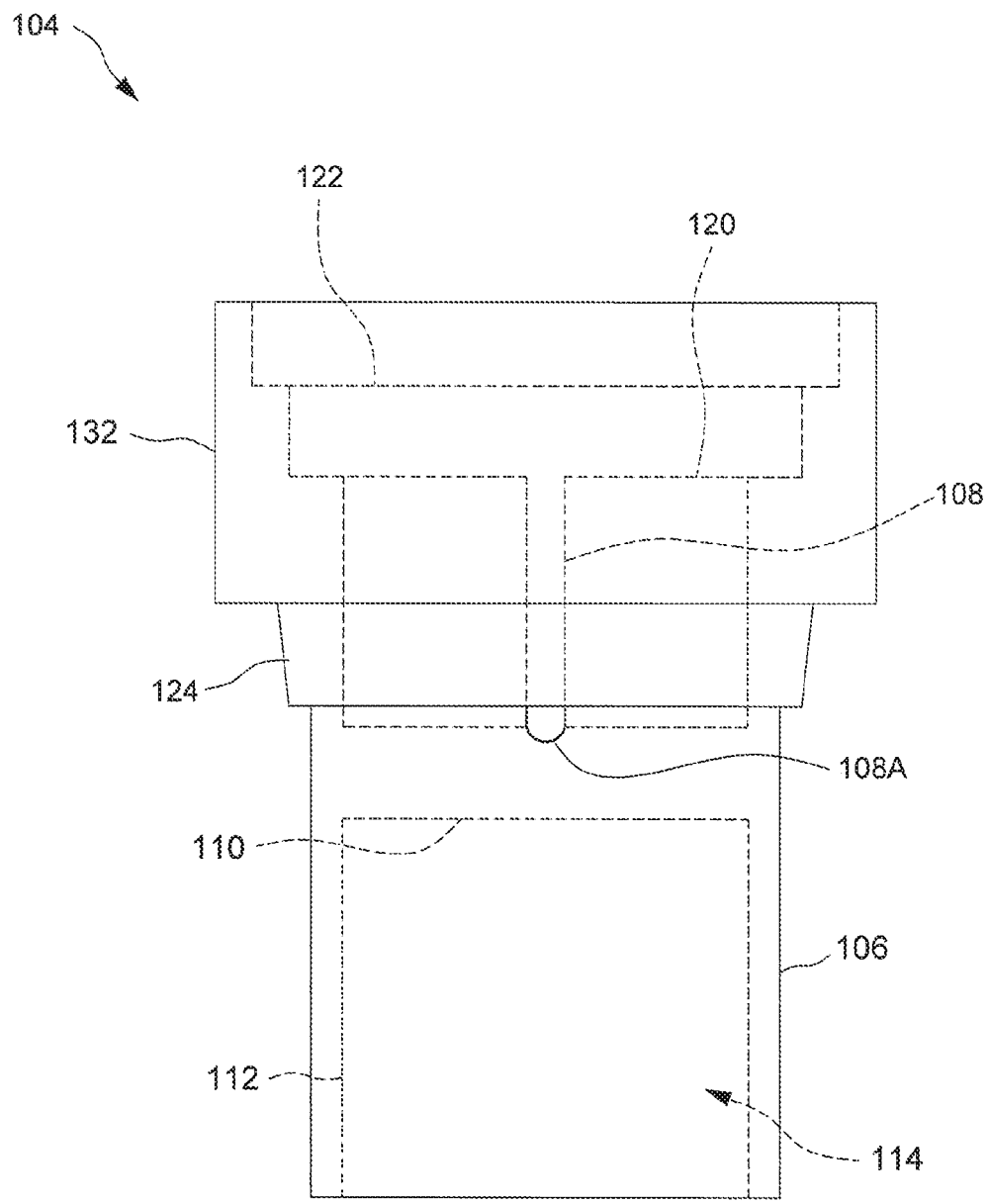
FIG. 3 is a side view illustrating a cover of the culture container shown in FIG. 1.

Embodiments described herein provide culture containers and systems and method that can facilitate the transfer of an organism of interest grown inside the culture containers. FIG. 1 is a perspective view illustrating an embodiment of a culture container 100, FIG. 2 is an exploded view of the culture container 100, and FIG. 3 is a side view illustrating a cover 104 of the culture container 100. Referring to FIGS. 1-3, the culture container 100 can be used for culturing and maintaining a population of an organism of interest. Examples of organisms that may be grown and maintained inside the culture container 100 may include, without limitation, *drosophila* species such as fruit flies, or any other insects that may be used as experimental models. The culture container 100 can include a tube 102 and a removable cover 104. The tube 102 may have any suitable shapes. Examples of shapes for the tube 102 can include, without limitation, a generally cylindrical shape (as shown), a truncated conical shape, a prismatic shape, etc. The tube 102 has a hollow interior, and two openings 103 and 105 respectively at two opposite ends that communicates with the hollow interior of the tube 102. To facilitate observation of an organism of interest enclosed inside the culture container 100, the tube 102 may be made of a transparent material, such as transparent glass or plastic.

The cover 104 is attachable to and removable from the opening 103 of the tube 102. The cover 104 includes a receptacle 106 and an inlet port 108. The receptacle 106 can be disposed at an inner side of the cover 104 facing the tube 102, and can be configured to hold a substance consumable by an organism of interest, such as nutritive substance, a drug substance and the like. According to an example of construction, the receptacle 106 may include a base surface 110 and a surrounding wall 112 connected with each other for at least partially delimiting a cavity 114 suitable for receiving the consumable substance. When the cover 104 is attached to and closes the opening 103 of the tube 102, the receptacle 106 is enclosed inside the tube 102 with the surrounding wall 112 protruding from the base surface 110 toward the other opening 105 of the tube 102.

The inlet port 108 communicates with the hollow interior of the tube 102 when the cover 104 is attached to and closes the opening 103 of the tube 102. A fluid substance may be flowed through the inlet port 108 into the culture container 100 while the cover 104 is attached to the tube 102. According to an example of construction, an outer side of the cover 104 opposite to that of the tube 102 may include a receiving cavity 116 having a sidewall 118, and the inlet port 108 can extend through the cover 104 and respectively open on the sidewall 118 of the receiving cavity 116 and at a side of the receptacle 106 on the inner side of the cover 104. For example, the inlet port 108 can have an opening 108A at a side of the receptacle 106, as shown in FIGS. 1 and 3. The inlet port 108 can thereby communicate with the receiving cavity 116. The receiving cavity 116 can have an enlarged size so as to facilitate flowing of a fluid substance into the receiving cavity 116, and then through the inlet port 108 to the interior of the culture container 100. The inlet port 108 and/or the opening 108A of the inlet port 108 inside the culture container 100 can be sufficiently small to prevent an organism of interest cultured inside the culture container 100 from escaping through the inlet port 108.

Referring to FIGS. 1-3, the cover 104 can further include one or more seal receiving surface disposed adjacent to the receiving cavity 116. According to an example of construction, two seal receiving surfaces 120 and 122 may be provided on the cover 104. The seal receiving surfaces 120 and 122 can extend generally parallel to each other peripherally around the receiving cavity 116. For example, the seal receiving surfaces 120 and 122 may be defined on flange portions projecting at different heights from the sidewall 118 of the receiving cavity 116. According to an embodiment, each of the seal receiving surfaces 120 and 122 can have an annular shape. However, any suitable shapes may be applied for the seal receiving surfaces 120 and 122. In use, each of the seal receiving surfaces 120 and 122 can receive the bonding of a sealing film for closing the receiving cavity 116 and preventing fluid passage through the inlet port 108 of the cover 104 into the hollow interior of the tube 102.

Any suitable technique may be applied to attach the cover 104 to the tube 102. According to an embodiment, the cover 104 may be attached to the tube 102 by interference fit between the cover 104 and the tube 102. For example, with reference to FIGS. 1 and 3, the cover 104 may include a coupling portion 124 that may be in frictional contact with a sidewall surface of the tube 102 when the cover 104 is assembled to close the opening 103. The coupling portion 124 can be exemplary inserted into the opening 103 in frictional contact with an inner surface region of the tube 102 adjacent to the opening 103. For facilitating installation and removal of the cover 104 on the tube 102, the frictional contact between the cover 104 and the tube 102 can be achieved on a tapered shape provided on the coupling portion 124 of the cover 104.

Figure 4:
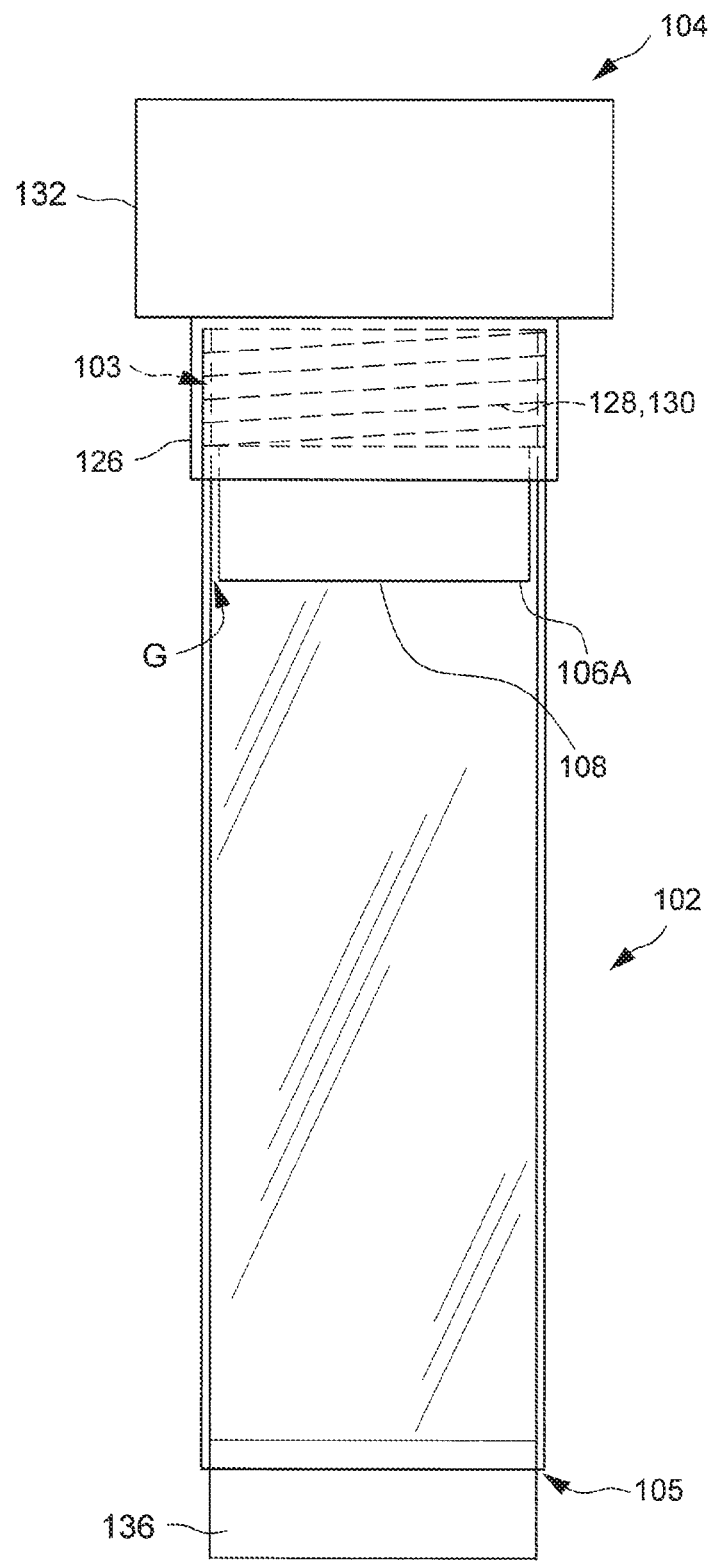
FIG. 4 is a schematic view illustrating a variant construction of a culture container.

FIG. 4 is a schematic view illustrating a variant construction in which the cover 104 may be attached to the tube 102 by thread engagement between the cover 104 and the tube 102. With reference to FIG. 4, the cover 104 may include a coupling portion 126 having a thread portion 128, and the tube 102 may have another thread portion 130 extending around the opening 103. The thread portions 128 and 130 may be engaged with each other for attaching the cover 104 to the tube 102.

Referring to FIGS. 1 and 4, when the cover 104 is attached to the tube 102, there may be a gap G between an inner sidewall surface of the tube 102 and the receptacle 106, the gap G extending along a height of the receptacle 106 to an end rim 106A of the receptacle 106. The tube 102 and the receptacle 106 can be dimensioned so that the gap G (especially at the end rim 106A of the receptacle 106) is sufficiently small to prevent passage of a cultured organism in the gap G.

Figure 5:
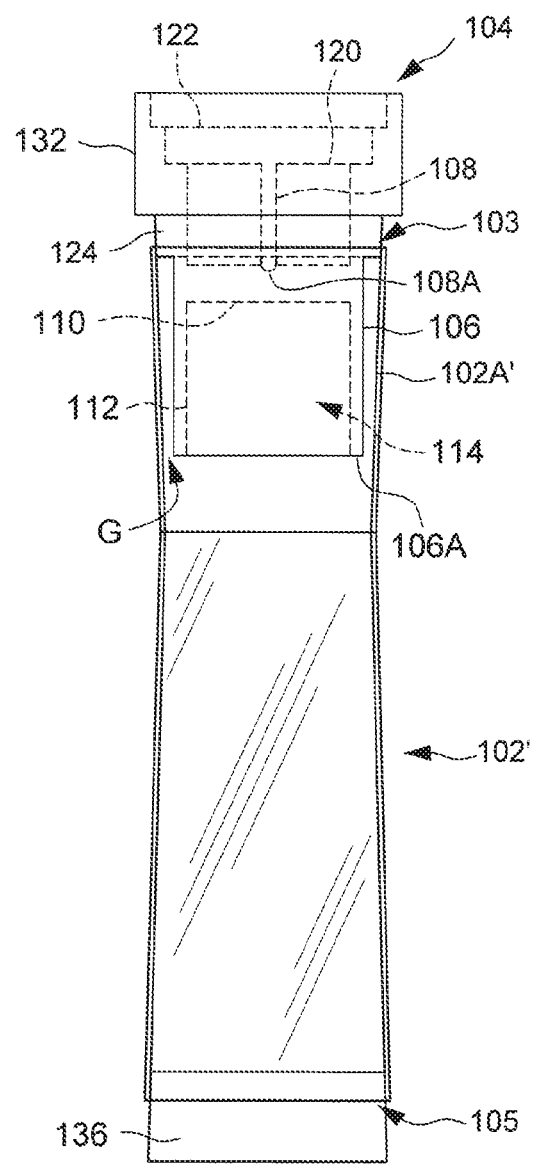
FIG. 5 is a side view illustrating another variant construction of a culture container.

FIG. 5 is a side view illustrating a variant construction in which the tube 102' may have a tapered portion 102A' adjacent to the receptacle 106 of the cover 104. The gap G can be defined between an inner sidewall of the tapered portion 102A' and the receptacle 106. Owing to the tapered portion 102A', the gap G may increasingly reduce toward the end rim 106A of the receptacle 106. In this manner, the gap G can be smallest at the end rim 106A to prevent passage of a cultured organism.

Referring to FIGS. 1-5, the cover 104 may further include a catch portion 132 that can project laterally from an outer side surface of the tube 102 when the cover 104 is attached to the tube 102. The catch portion 132 may extend continuously along a circumference of the cover 104, or may project locally on a periphery of the cover 104. The catch portion 132 can facilitate grasping of the cover 104 for installation and removal of the cover 104 on the tube 102.

Referring again to FIGS. 1 and 2, the culture container 100 may further include an air-permeable plug 136 that may be detachably installed to close the opening 105 of the tube 102. The air-permeable plug 136 can prevent the cultured organism of interest from escaping the culture container 100 through the opening 105 of the tube 102 while allowing air passage for breathing of the cultured organism. The air-permeable plug 136 can include a breathable material. Examples of materials for the air-permeable plug 136 may include, without limitation, cotton, breathable fibers, porous or perforate materials, and the like.

According to at least an embodiment, the culture container 100 described herein may be implemented as a culture vial having an elongate shape. For example, the tube 102 may have a length between about 5 cm and about 20 cm. The tube 102 may further exemplary have a radius between about 0.5 cm and about 6 cm. The cover 104 may have a height between about 1 cm and about 10 cm. Moreover, the cover 104 may have a radius between about 0.5 cm and about 6 cm.

However, it will be appreciated that the culture container 100 is not limited to vial embodiments, and may take other forms. For example, the culture container 100 described herein may also be implemented as a culture bottle for growing a greater population of the organism of interest.

Figure 6:
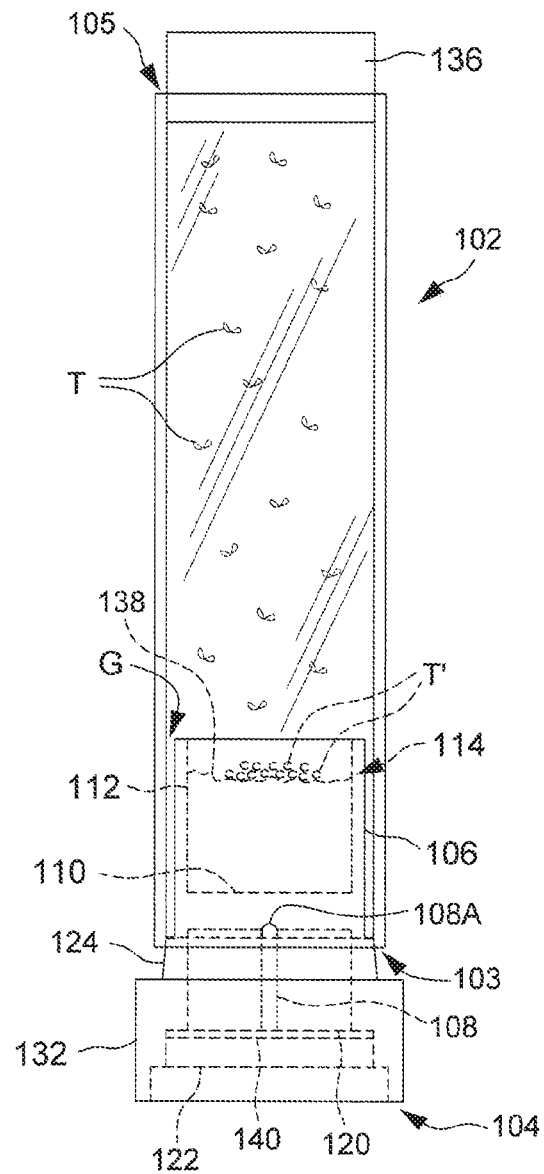
FIG. 6 is a schematic view illustrating exemplary use of the culture container for culturing and maintaining a population of an organism of interest.

FIG. 6 is a schematic view illustrating exemplary use of the culture container 100 for culturing and maintaining a population of an organism of interest T. Examples of the organism T may include, without limitation, fruit flies or any other insects of interest. The organism enclosed in the culture container 100 may include an adult form and a non-adult form, such as eggs, larvae and/or pupae. The culture container 100 may be used to culture a population of the organism of interest T with the cover 104 closing the opening 103 of the tube 102 and the air-permeable plug 136 closing the opening 105 of the tube 102 opposite to the cover 104. The receptacle 106 of the cover 104 may retain a substance 138 consumable by the organism of interest T grown and enclosed inside the culture container 100. The consumable substance 138 may include, without limitation, a nutritive substance, a drug substance and the like. In addition, the receptacle 106 of the cover 104 may receive new generations T' of the organism of interest, which may include, without limitation, a non-adult form of the organism such as eggs, larvae and/or pupae. For example, the new generations T' of the organism of interest may adhere to the consumable substance 138 and/or the wall 112 of the receptacle 106. Moreover, a sealing film 140 may be bonded to one of the two seal receiving surfaces 120 and 122 (e.g., the seal receiving surface 120 as shown) to prevent introduction of undesirable substances or contaminants through the inlet port 108 of the cover 104 into the interior of the culture container 100. To facilitate air passage through the air-permeable plug 136 into the culture container 100, the culture container 100 may be disposed with the cover 104 at the bottom and the air-permeable plug 136 at the top while culturing the organism of interest T.

As the organism of interest T is cultured inside the culture container 100 over a period of time, new generations T' of the organism as well as dead organic matter may accumulate inside the culture container 100. As a result, a transfer to a new culture container may be needed for continuing the culture of the organism of interest T.

Figure 7:
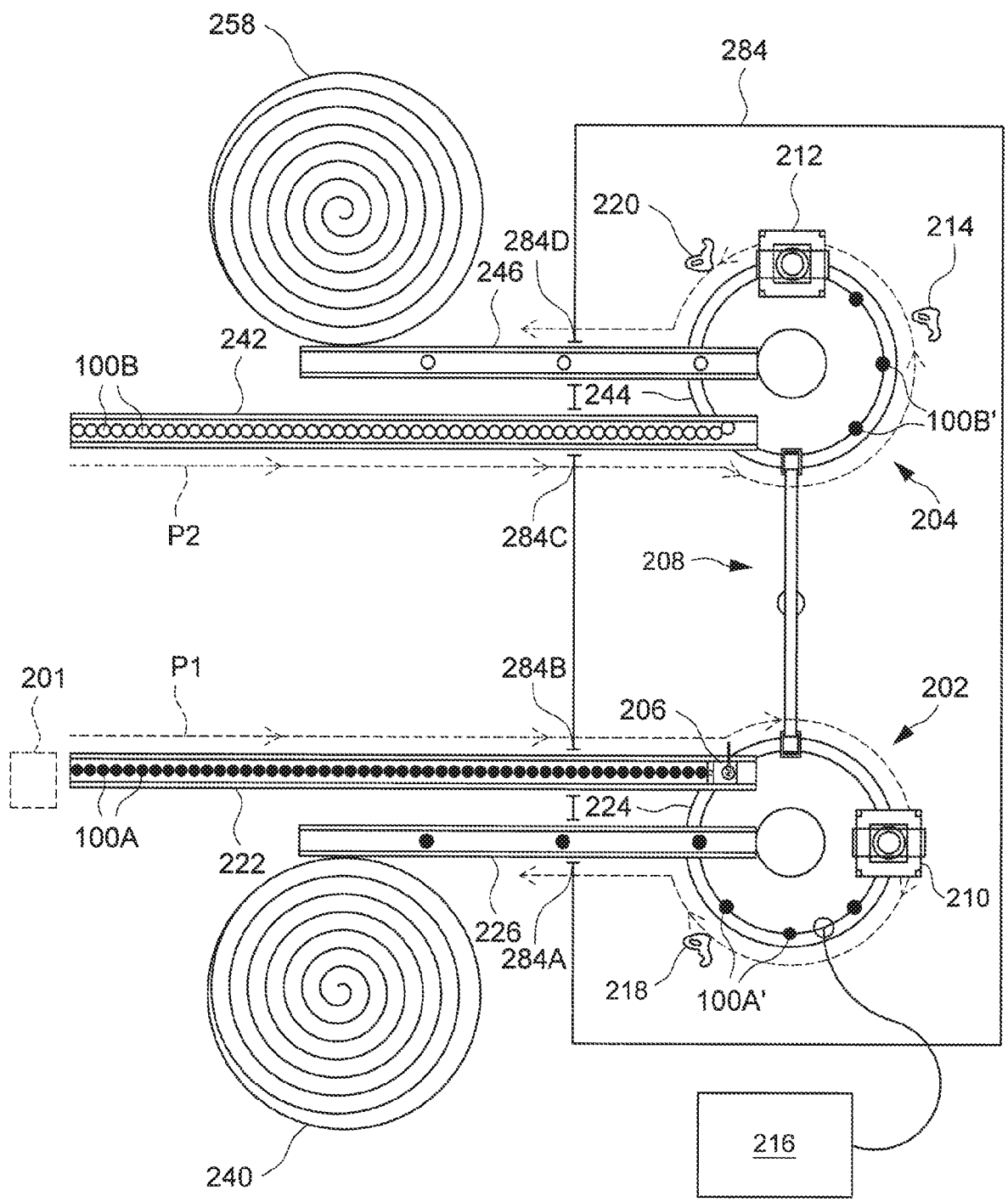
FIG. 7 is a simplified view illustrating an automated transfer system operable to transfer a cultured organism of interest between a plurality of culture containers.
Figure 16:
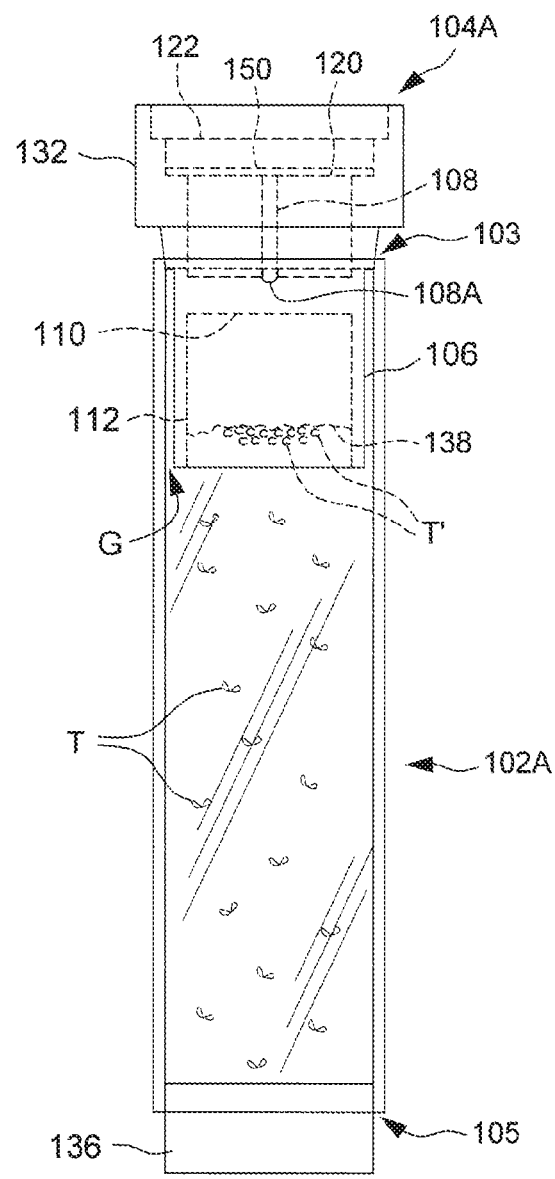
FIG. 16 is a schematic view illustrating a first culture container enclosing an organism of interest initially provided to the transfer system.
Figure 17:
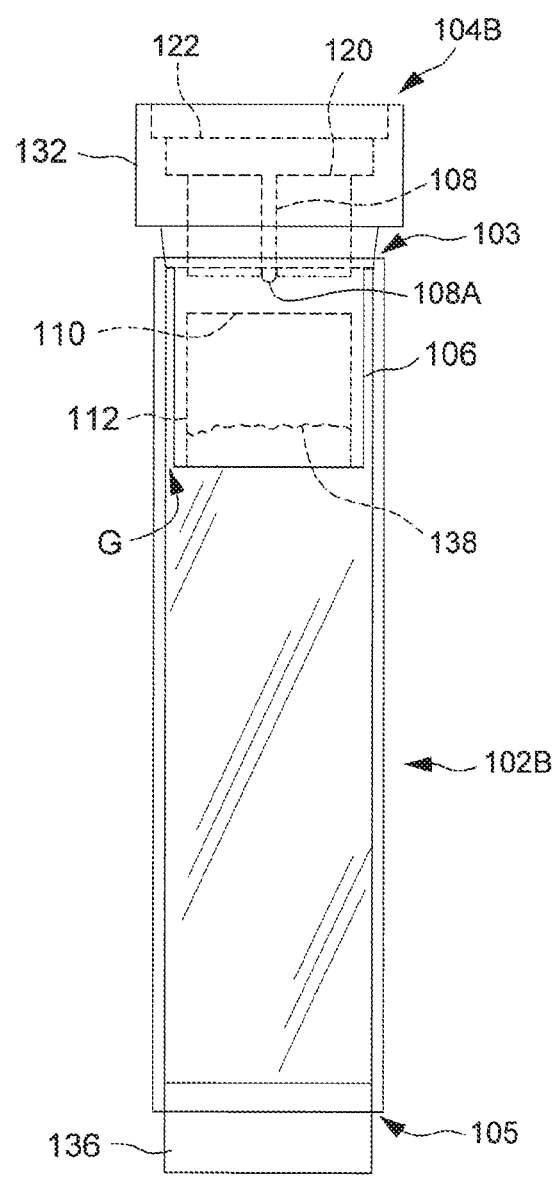
FIG. 17 is a schematic view illustrating an example of a clean second culture container initially provided to the transfer system.

FIG. 7 is a simplified view illustrating an automated transfer system 200 operable to transfer a cultured organism of interest between a plurality of culture containers 100A and 100B. Each of the culture containers 100A and 100B can have the same construction as the culture container 100 described previously. FIG. 16 is a schematic view illustrating an example of one culture container 100A initially provided to the transfer system 200, and FIG. 17 is a schematic view illustrating an example of one culture container 100B initially provided to the transfer system 200. Referring to FIG. 16, each of the culture containers 100A initially provided contains a culture of an organism of interest T, which may be exemplary fruit flies or other insects. The initial culture container 100A includes a tube 102A that is respectively closed with a cover 104A at one end and an air-permeable plug 136 at the other opposite end. The cover 104A can have the same construction as the cover 104 described previously, and can include the inlet port 108 and the receptacle 106 received inside the tube 102A of the culture container 100A. The receptacle 106 of the cover 104A may hold a substance 138 consumable by the organism of interest T (e.g., including a nutritive substance, a drug substance and the like), and new generations T' of the organism of interest T, which can include a non-adult form of the organism such as eggs, larvae and/or pupae.

Referring to FIG. 17, each of the culture containers 100B initially provided is a clean culture container containing no culture of organism. Likewise, the initial culture container 100B includes a tube 102B that is respectively closed with a cover 104B at one end and an air-permeable plug 136 at the other opposite end. The cover 104B can have the same construction as the cover 104 described previously, and can include the inlet port 108 and the receptacle 106 received inside the initial culture container 100B. The receptacle 106 of the cover 104B may hold a substance 138 consumable by the organism of interest.

Referring to FIG. 7, an embodiment of the automated transfer system 200 can include two conveyor systems 202 and 204, an anesthetization unit 206, an exchanging unit 208, two sealing units 210 and 212, a reading unit 214, a printing unit 216, and two inspection units 218 and 220.

The conveyor system 202 can define a transport path P1 along which the culture containers 100A may be conveyed for processing. According to an embodiment, the conveyor system 202 can include a container supplying part 222, a rotary platform 224 and a container discharging part 226. The container supplying part 222 may include a ramp or a conveying belt, and can transport the culture containers 100A in a row. The container supplying part 222 can deliver each initially provided culture container 100A to the rotary platform 224 with the cover 104A on top of the tube 102A.

According to an implementation, the culture containers 100A may be manually positioned so that the cover 104A of each culture container 100A is on top of the tube 102A thereof. According to another implementation, a machine equipment may be provided before the conveyor system 202 to flip the culture containers 100A so that the cover 104A of each culture container 100A is on top of the tube 102A thereof. For example, the culture containers 100A may be initially placed on a support frame, and a flipping unit 201 (e.g., including robot arms) may be provided to turn over the support frame and culture containers 100A placed thereon so that the cover 104A of each culture container 100A is on top of the tube 102A.

Figure 8:
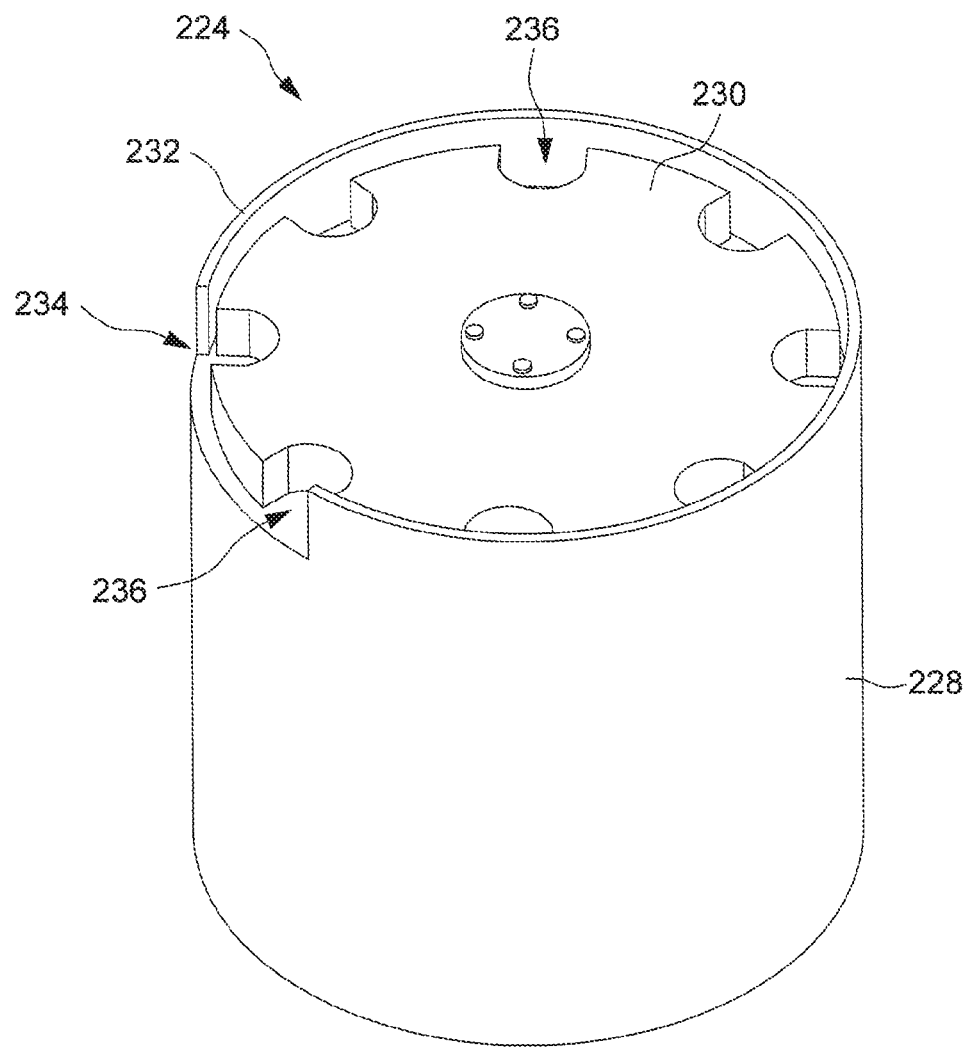
FIG. 8 is a perspective view schematically illustrating an embodiment of a rotary platform provided in a first conveyor system of the transfer system shown in FIG. 7.

In conjunction with FIGS. 7 and 16, FIG. 8 is a perspective view schematically illustrating the rotary platform 224. Referring to FIGS. 7, 8 and 16, the rotary platform 224 may include a fixed base 228, and a rotary plate 230 pivotally connected with the fixed base 228. The fixed base 228 may include a sidewall 232 that extends around the rotary plate 230 and has an opening 234 through which culture containers may be loaded on and/or unloaded from the rotary platform 224. The rotary plate 230 can have a plurality of slots 236 that are disposed along a circle spaced apart from one another. The slot 236 may be shaped and sized so as to receive one culture container 100A, especially the tube 102A thereof. The tube 102A of each culture container 100A may be loaded into one slot 236 of the rotary plate 230 through the opening 234, and the rotary plate 230 then can rotate to convey the tube 102A placed in the slot 236 along an arcuate portion of the transport path P1 from the container supplying part 222 through the exchanging unit 208 to the container discharging part 226.

The container discharging part 226 can include a ramp or a conveying belt. The container discharging part 226 can be disposed downstream of the exchanging unit 208 along the transport path P1, and convey processed culture containers 100A' from the rotary platform 224 toward a receiving tray 240.

Figure 9:
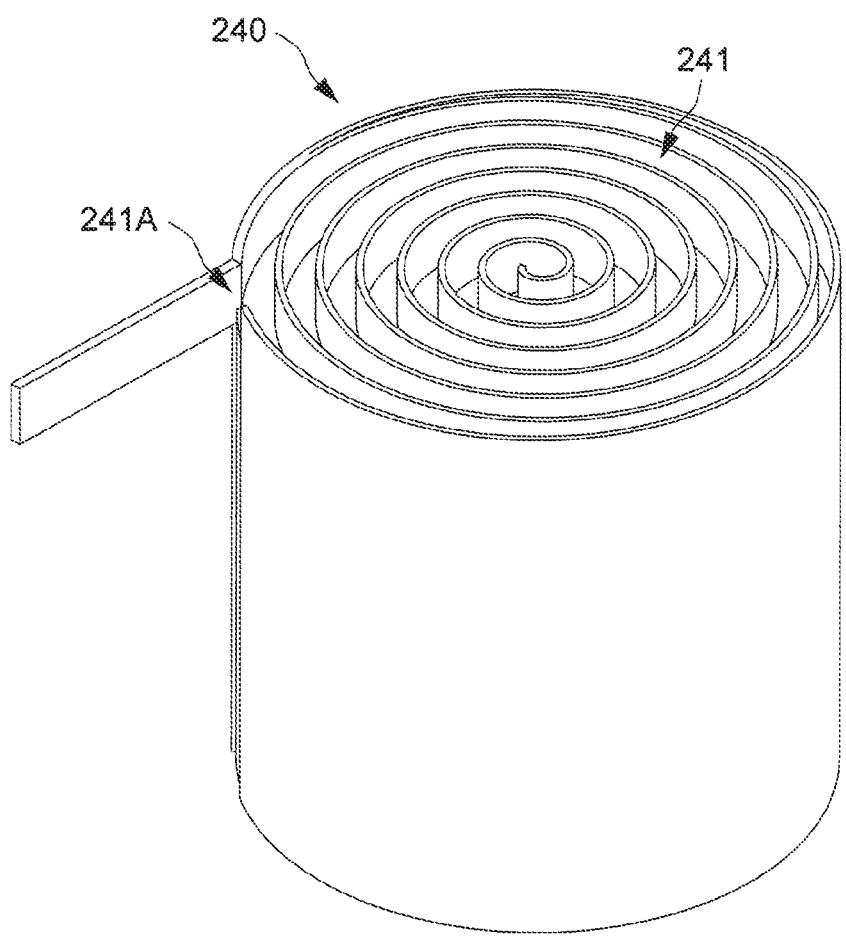
FIG. 9 is a perspective view illustrating a receiving tray provided in the transfer system shown in FIG. 7.

FIG. 9 is a perspective view illustrating the receiving tray 240. The tray 240 can include a spiral track 241 for receiving the processed culture containers 100A'. The processed containers 100A' may be pushed to travel through an opening 241A of the receiving tray 240 and enter the spiral track 241 for temporary storage. The shape of the spiral track 241 may facilitate discharge of the processed culture containers 100A' from the container discharging part 226.

Referring again to FIG. 7, the conveyor system 204 can define a transport path P2 along which the culture containers 100B may be conveyed for processing. According to an embodiment, the conveyor system 204 can be similar to the conveyor system 202 in construction, and can include a container supplying part 242, a rotary platform 244 and a container discharging part 246. The container supplying part 242 may include a ramp or a conveying belt, and can transport the culture containers 100B in a row. The container supplying part 242 can deliver each culture container 100B to the rotary platform 244 with the cover 104B on top of the tube 102B.

Figure 10:
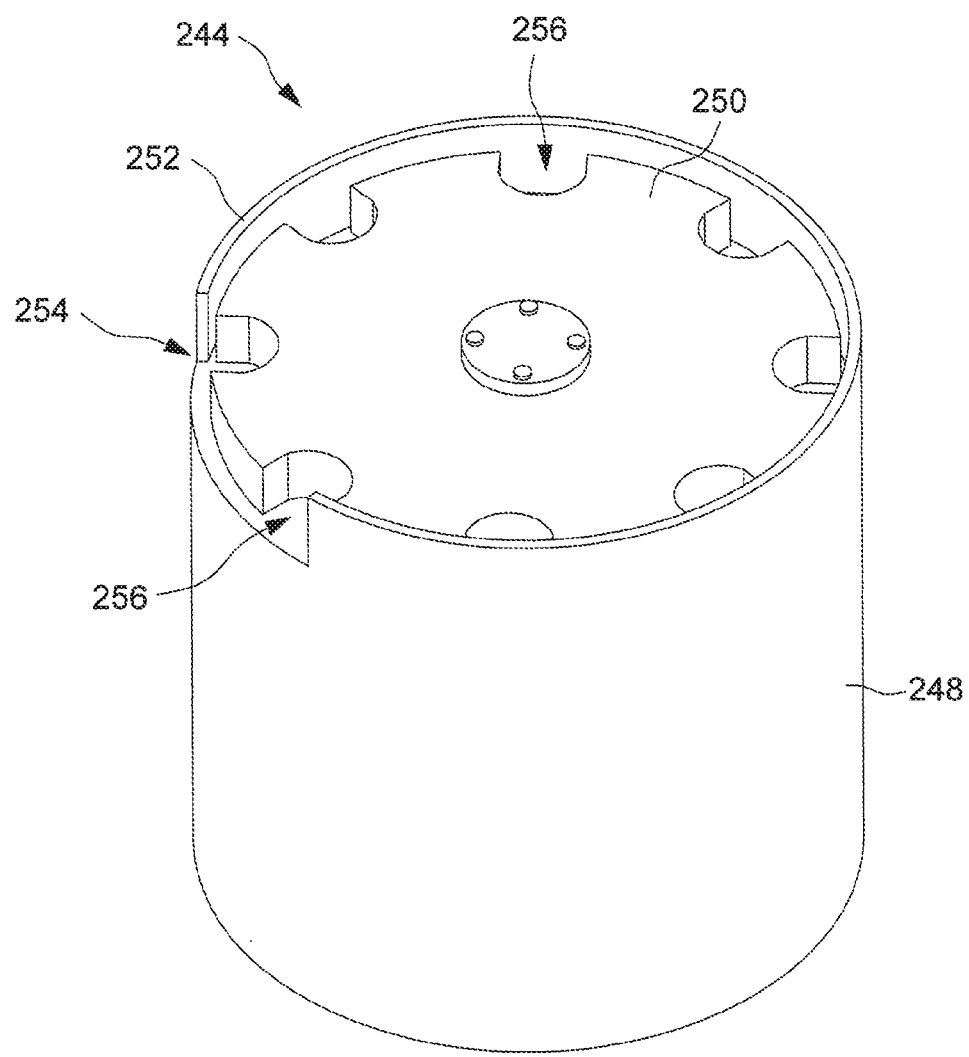
FIG. 10 is a perspective view schematically illustrating an embodiment of a rotary platform provided in a second conveyor system of the transfer system shown in FIG. 7.

In conjunction with FIGS. 7 and 17, FIG. 10 is a perspective view schematically illustrating the rotary platform 244. Referring to FIGS. 7, 10 and 17, the rotary platform 244 may include a fixed base 248, and a rotary plate 250 pivotally connected with the fixed base 248. The fixed base 248 may include a sidewall 252 that extends around the rotary plate 250 and has an opening 254 through which culture containers may be loaded on and/or unloaded from the rotary platform 244. The rotary plate 250 can have a plurality of slots 256 that are disposed along a circle spaced apart from one another. The slot 256 may be shaped and sized so as to receive one culture container 100B, especially the tube 102B thereof. The tube 102B of each culture container 100B may be loaded into one slot 256 of the rotary plate 250 through the opening 254, and the rotary plate 250 then can rotate to convey the tube 102B placed in the slot 256 along an arcuate portion of the transport path P2 from the container supplying part 242 through the exchanging unit 208 to the container discharging part 246.

The container discharging part 246 can include a ramp or a conveying belt. The container discharging part 246 can be disposed downstream of the exchanging unit 208 along the transport path P2, and convey processed culture containers 100B' from the rotary platform 244 toward a receiving tray 258.

Figure 11:
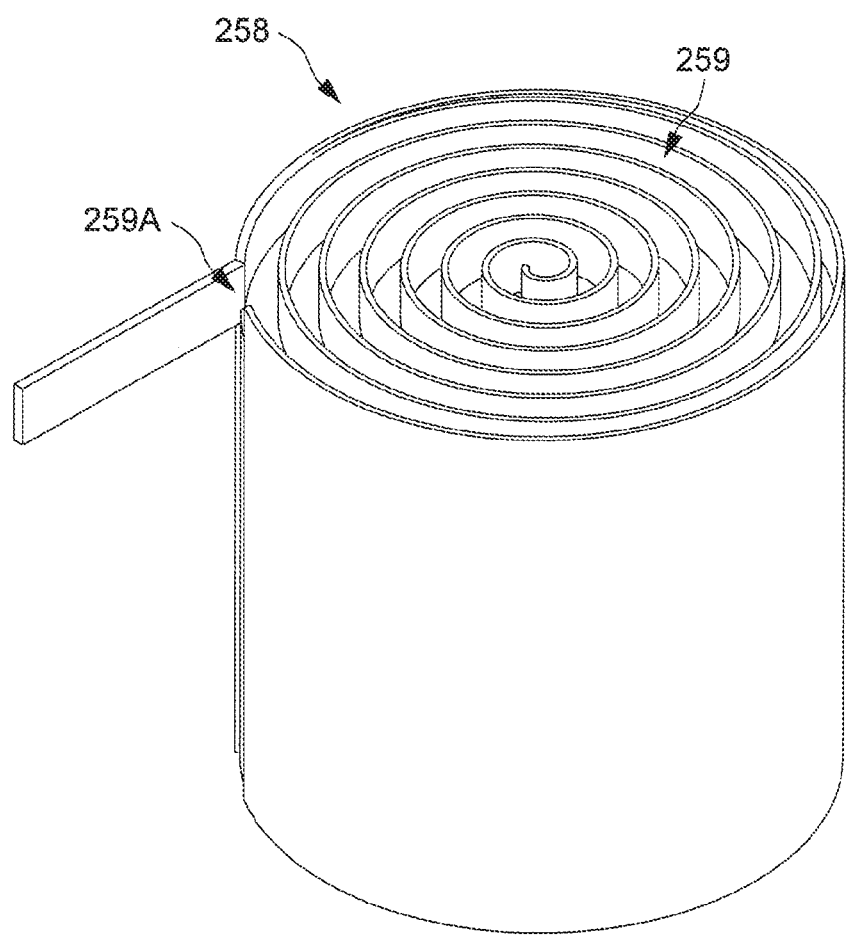
FIG. 11 is a perspective view illustrating another receiving tray provided in the transfer system shown in FIG. 7.

FIG. 11 is a perspective view illustrating the receiving tray 258. The tray 258 may be similar to the receiving tray 240, and can include a spiral track 259 for receiving the processed culture containers 100B'. The processed containers 100B' may be pushed to travel through an opening 259A of the receiving tray 258 and enter the spiral track 259 for temporary storage. The shape of the spiral track 259 may facilitate discharge of the processed culture containers 100B' from the container discharging part 246.

Referring to FIG. 7, the anesthetization unit 206 may be disposed adjacent to the conveyor system 202, and upstream of the exchanging unit 208 along the transport path P1. The anesthetization unit 206 is operable to anesthetize the organism of interest T enclosed inside each culture container 100A. According to an implementation, the anesthetization unit 206 may deliver an anesthetic substance into each culture container 100A through the inlet port 108 (better shown in FIG. 16) provided on the cover 104A for anesthetizing the organism of interest T. A portion of the anesthetized organism, mostly its adult form, can then fall on the air-permeable plug 136, e.g., by gravity action.

Figure 12:
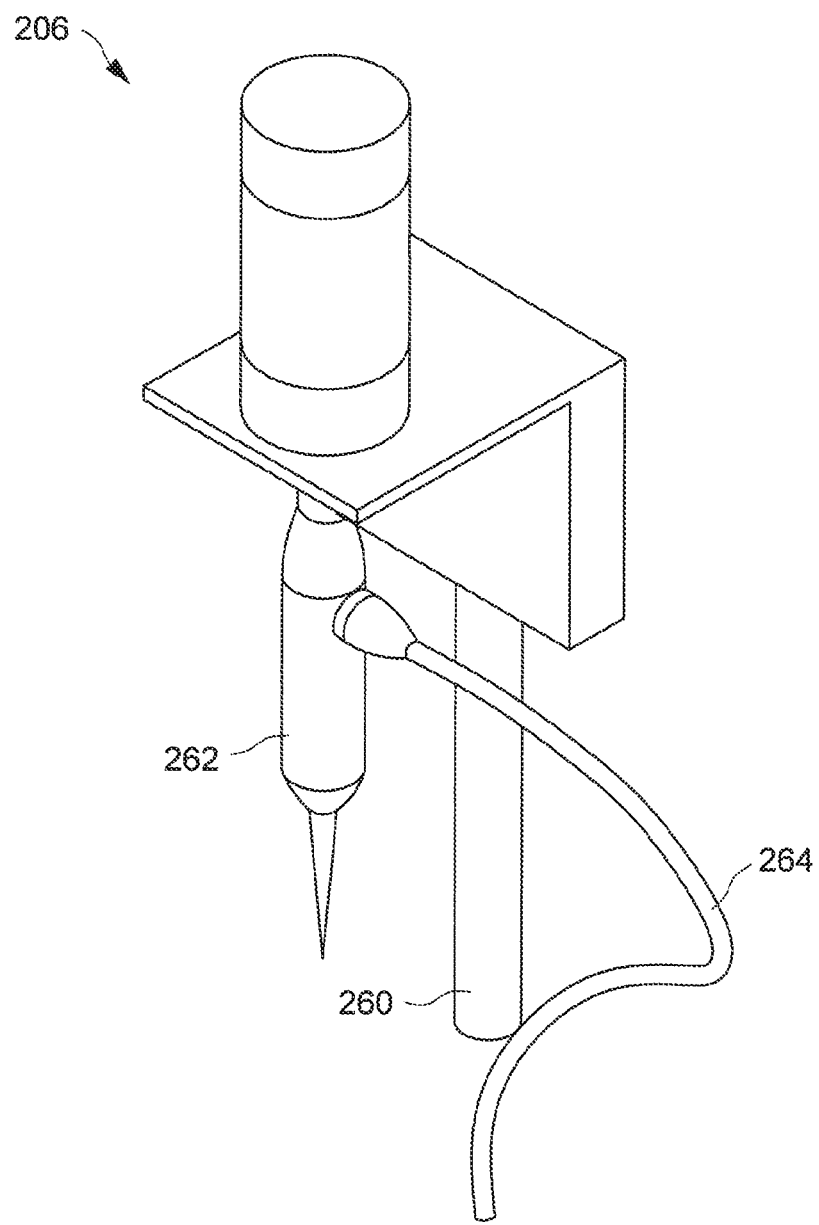
FIG. 12 is a perspective view schematically illustrating an anesthetization unit provided in the transfer system shown in FIG. 7.

In conjunction with FIG. 7, FIG. 12 is a perspective view schematically illustrating a portion of the anesthetization unit 206. Referring to FIGS. 7, 12 and 16, according to an embodiment, the anesthetization unit 206 can include a fixed support frame 260, and a nozzle 262 and a conduit 264 connected with each other. An anesthetic substance, e.g., dioxide carbon, may be flowed along the conduit 264 to the nozzle 262. The nozzle 262 can be movably connected with the fixed frame 260 for upward and downward movement. The nozzle 262 can move downward to a lower position adjacent to the culture container 100A for facilitating delivery of the anesthetic substance through the cover 104A into the interior of the culture container 100A, and move upward to an upper position to clear the way for displacement of the culture container 100A.

As better illustrated in FIG. 16, the culture container 100A processed at the anesthetization unit 206 may have a sealing film 150 that is bonded to the cover 104A (e.g., the seal receiving surface 120 thereof) for preventing fluid passage through the inlet port 108 into the hollow interior of the culture container 100A. According to an embodiment, the nozzle 262 of the anesthetization unit 206 may further include a shape adapted to pierce the sealing film 150 before delivering the anesthetic substance into the culture container 100A.

According to an example of implementation, the anesthetization unit 206 may be disposed adjacent to the rotary platform 224, as shown in FIG. 7. Once the anesthetic substance is introduced into the culture container 100A, the rotary platform 224 may convey the culture container 100A away from the anesthetization unit 206 toward the exchanging unit 208.

Figure 13:
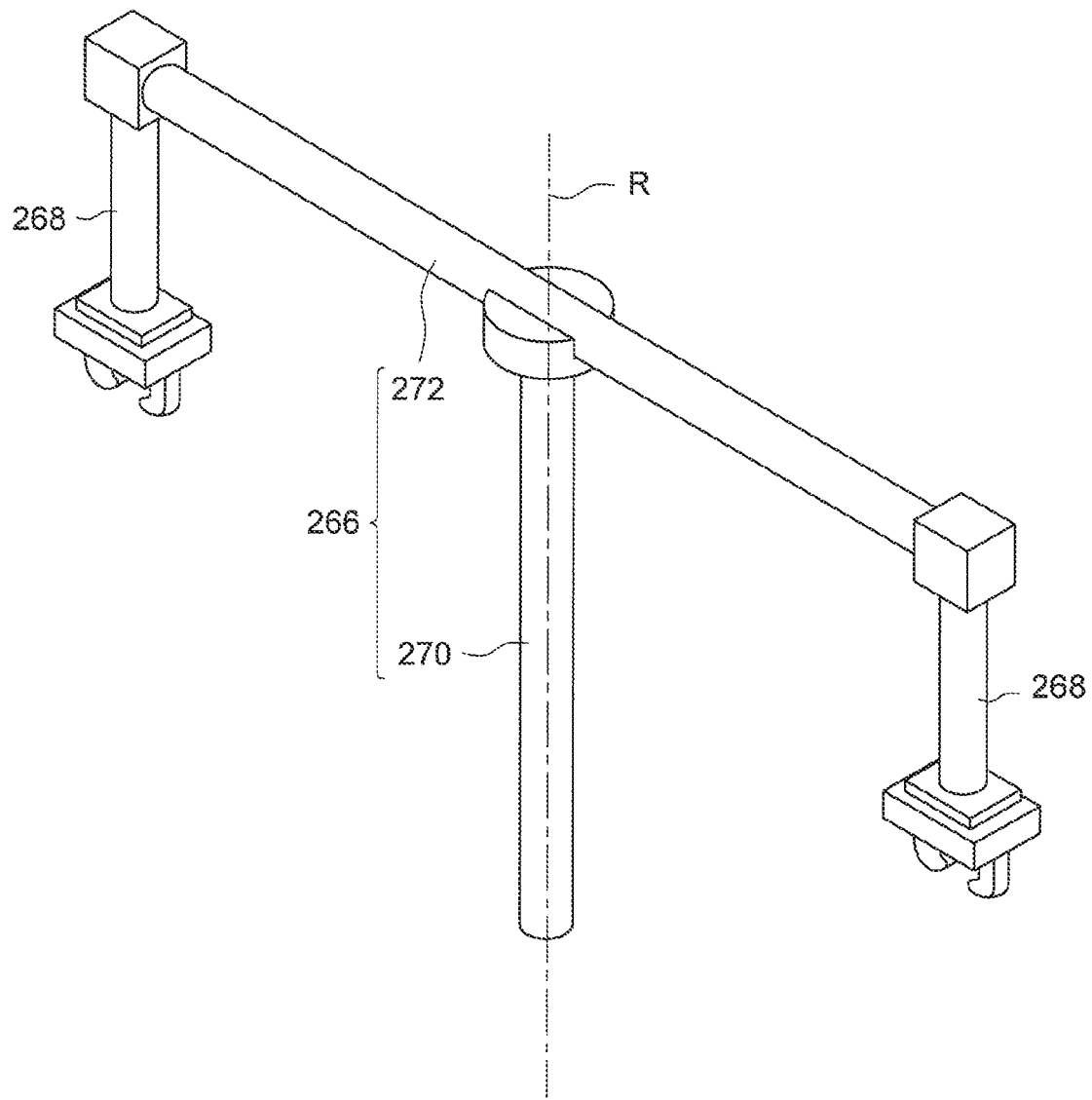
FIG. 13 is a perspective view schematically illustrating an exchanging unit provided in the transfer system shown in FIG. 7.

In conjunction with FIG. 7, FIG. 13 is a perspective view schematically illustrating an embodiment of the exchanging unit 208. Referring to FIGS. 7 and 13, the exchanging unit 208 can be disposed downstream of the anesthetization unit 206 along the transport path P1 and between the two conveyor systems 202 and 204, which can respectively carry the culture containers 100A and 100B toward the exchanging unit 208 with the covers 104A and 104B respectively on top of the tubes 102A and 102B. The exchanging unit 208 is operable to interchange the covers 104A and 104B between two culture containers 100A and 100B, so that the cover 104A initially attached to the tube 102A of the culture container 100A becomes attached to the tube 102B of the initially provided culture container 100B, and the cover 104B initially attached to the tube 102B of the culture container 100B becomes attached to the tube 102A of the initially provided culture container 100A. More specifically, the exchanging unit 208 may be operable to respectively separate the two covers 104A and 104B from the two tubes 102A and 102B, switch the two covers 104A and 104B with respect to the two tubes 102A and 102B, and respectively attach the cover 104A to the tube 102B and the cover 104B to the tube 102A.

According to an embodiment, the exchanging unit 208 can include a rotary part 266 and two arms 268. The rotary part 266 can exemplary include a support stem 270 and a transversal bar 272 fixedly connected with each other. The support stem 270 may be rotatable about a pivot axis R, and the transversal bar 272 may extend substantially perpendicular to the pivot axis R. The two arms 268 may be attached to the transversal bar 272 of the rotary part 266 at two diametrically opposite positions relative to the pivot axis R of the rotary part 266. The two arms 268 can be configured to respectively grasp and hold the two covers 104A and 104B at the catch portions 132 thereof. Each of the two arms 268 is operable to separate or attach one cover 104A or 104B with respect to one tube 102A or 102B, and the rotary part 266 is rotatable to switch the two covers 104A and 104B with respect to the two tubes 102A and 102B.

According to an example of implementation, in addition to the rotation about the pivot axis R, the rotary part 266 and the two arms 268 may further be slidable in unison along the pivot axis R. The rotary part 266 and the two arms 268 can slide upward along the pivot axis R to respectively separate the covers 104A and 104B with respect to the tube 102A and 102B, rotate about the pivot axis R to move and switch the two covers 104A and 104B with respect to the two tubes 102A and 102B which are respectively kept stationary on the rotary platforms 224 and 244, and then slide downward to respectively attach the cover 104A to the tube 102B and the cover 104B cover to the tube 102A.

Referring again to FIG. 7, after switching of the two covers 104A and 104B at the exchanging unit 208, each culture container 100A becomes a culture container 100A' comprised of the cover 104B attached to the tube 102A, and each culture container 100B becomes a culture container 100B' comprised of the cover 104A attached to the tube 102B. The culture containers 100A' and 100B' are respectively illustrated in FIGS. 18 and 19. The culture container 100A' can be further transported by the conveyor system 202 along the transport path P1 for processing through the sealing unit 210 and the printing unit 216, while the culture container 100B' can be further transported by the conveyor system 204 along the transport path P2 for processing through the sealing unit 212 and the reading unit 214.

The sealing unit 210 can be disposed adjacent to the rotary platform 224 downstream of the exchanging unit 208 along the transport path P1, and the sealing unit 212 can be disposed adjacent to the rotary platform 244 downstream of the exchanging unit 208 along the transport path P2. The sealing unit 210 can bond a sealing film on the cover 104B attached to the tube 102A (e.g., on the seal receiving surface 120 thereof), and the sealing unit 212 can bond another sealing film on the cover 104A attached to the tube 102B (e.g., on the seal receiving surface 122 thereof).

Figure 14:
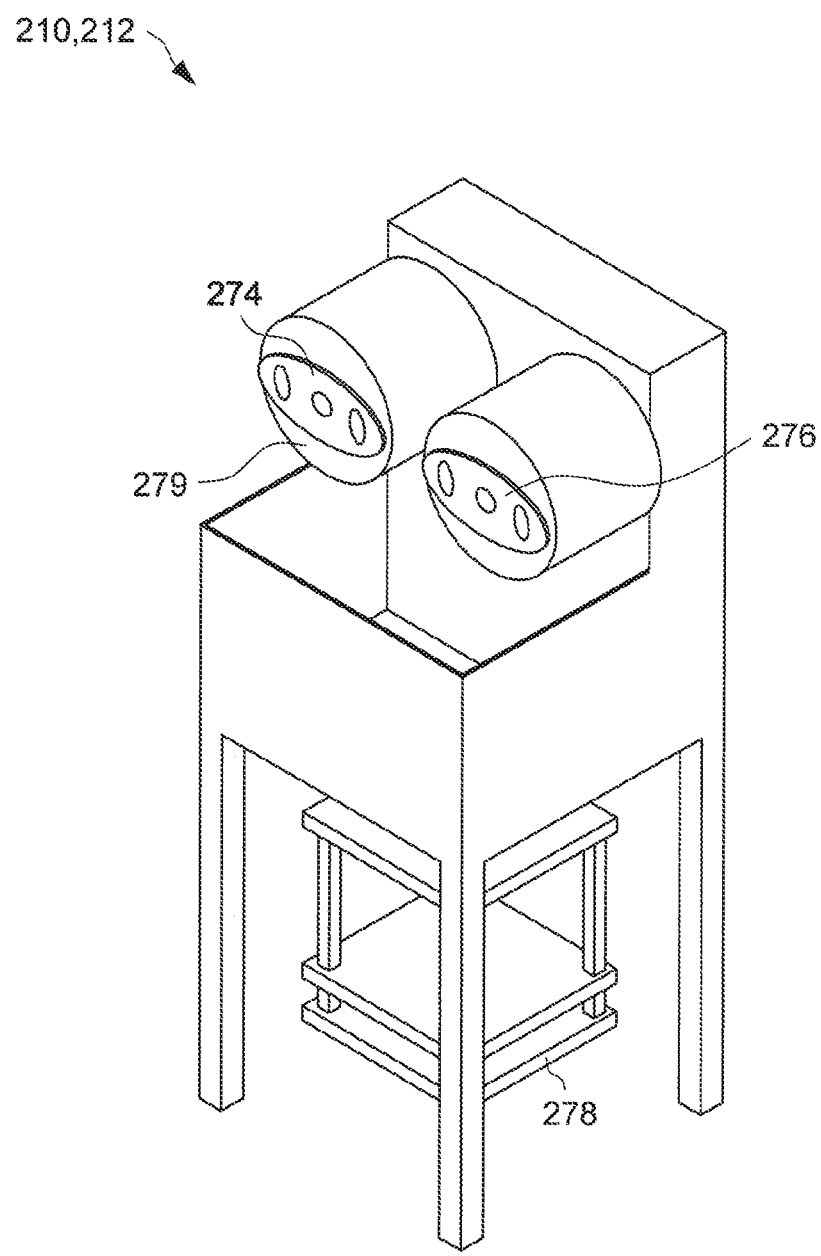
FIG. 14 is a schematic view illustrating an example of construction for a sealing unit provided in the transfer system shown in FIG. 7.

In conjunction with FIG. 7, FIG. 14 is a schematic view illustrating an example of construction for each of the sealing units 210 and 212. Each of the sealing unit 210 and 212 can include a feed drum 274, a take-up drum 276 and a heater 278. A roll of a sealing film 279 may be wound around the feed drum 274 and connected with the take-up drum 276. The take-up drum 276 can rotate to unwind the sealing film 279 from the feed drum 274, and the heater 278 can operate to thermally bond the sealing onto the seal receiving surface 120 or 122 of the cover 104A or 104B.

Referring again to FIG. 7, the reading unit 214 can be disposed adjacent to the transport path P2 downstream of the exchanging unit 208, e.g., upstream (as shown) or downstream of the sealing unit 212 along the transport path P2. Examples of the reading unit 214 may include a scanning device. The reading unit 214 can read an identification code on the cover 104A attached to the tube 102B of the culture container 100B'. The identification code acquired by the reading unit 214 may include information regarding the organism of interest T initially kept in the culture container 100A comprised of the tube 102A and the cover 104A.

The printing unit 216 can be disposed adjacent to the transport path P1 downstream of the exchanging unit 208, e.g., downstream (as shown) or upstream of the sealing unit 210 along the transport path P1. The printing unit 216 can print an identification code on the cover 104B attached to the tube 102A of the culture container 100A' according to the code read on the cover 104A by the reading unit 214. The identification code may contain information such as a description of the organism of interest T, the date of transfer, and other useful information. In this manner, the chain of transfer for the cultured organism of interest T can be suitably traced.

Figure 15:
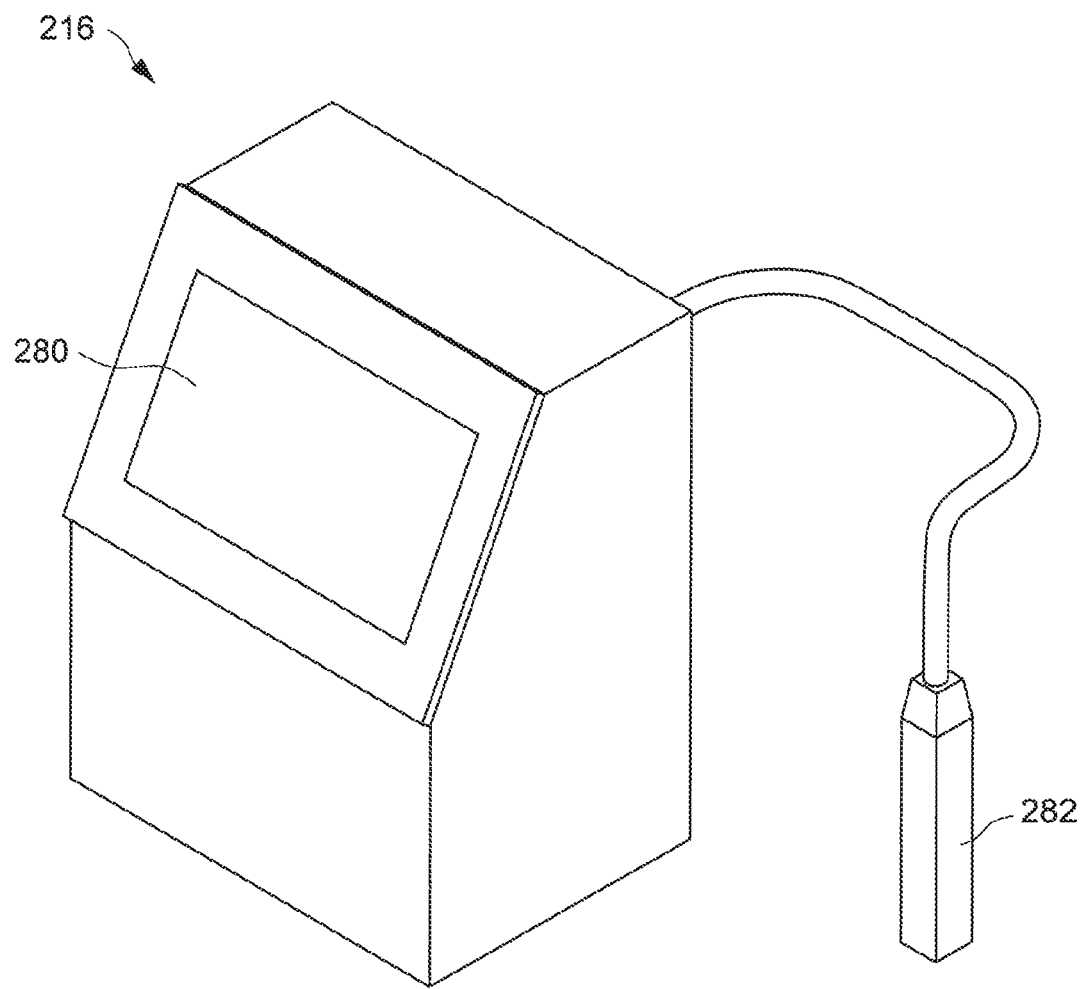
FIG. 15 is a perspective view schematically illustrating a printing unit provided in the transfer system shown in FIG. 7.

In conjunction with FIG. 7, FIG. 15 is a perspective view schematically illustrating the printing unit 216. The printing unit 216 may include a screen 280 and a printing gun 282. The screen 280 may display various information or settings for the printing unit 216. The printing unit 216 may receive data corresponding to the code read by the reading unit 214 on the cover 104A attached to the tube 102B, and can print a corresponding identification code on the cover 104B attached to the tube 102A via the printing gun 282.

Referring again to FIG. 7, the inspection units 218 and 220 can include scanning devices. The inspection unit 218 can be disposed adjacent to the rotary platform 224 downstream of the printing unit 216 and the sealing unit 210 along the transport path P1, e.g., before the container discharging part 226. The inspection unit 220 can be disposed adjacent to the rotary platform 244 downstream of the reading unit 214 and the sealing unit 212 along the transport path P2, e.g., before the container discharging part 246. The inspection units 218 and 220 can respectively read information on the cover 104B attached to the tube 102A and information on the cover 104A attached to the tube 102B, and verify that they are consistent before the culture containers 100A' and 100B' are discharged toward the receiving trays 240 and 258 via the container discharging parts 226 and 246.

In the automated transfer system 200, the exchange of the covers 104A and 104B between two culture containers 100A and 100B can be performed in a confined environment so as to prevent introduction of contaminants in the culture containers. Referring to FIG. 7, this confined environment can be exemplary provided by a pressurized chamber 284, which can enclose at least partially the conveyor systems 202 and 204 (including the rotary platforms 224 and 244), the anesthetization unit 206, the exchanging unit 208, the sealing units 210 and 212, the reading unit 214 and the inspection units 218 and 220. The pressurized chamber 284 can include a plurality of openings 284A, 284B, 284C and 284D for passage of the container discharging part 226, the container supplying part 222, the container supplying part 242 and the container discharging part 246, respectively. In this manner, the conveyor systems 202 and 204 can respectively convey culture containers into and out of the pressurized chamber 284. The pressurized chamber 284 can maintain an internal pressure higher than the pressure of an outer environment to prevent introduction of contaminants into the pressurized chamber 284.

In conjunction with FIGS. 7-21, FIG. 22 is a flowchart of method steps executable by the automated transfer system 200 for transferring an organism of interest T from the culture containers 100A to the culture containers 100B. In initial step 302, the culture containers 100A enclosing an organism of interest T can be provided on the conveyor system 202. Examples of the organism of interest T can include, without limitation, fruit flies or other insects. The organism of interest T enclosed in each culture container 100A can include an adult form, and a non-adult form such as eggs, larvae and/or pupae. Each culture container 100A can include the tube 102A, the cover 104A closing the opening 103 of the tube 102A, and the air-permeable plug 136 closing the opening 105 of the tube 102A. The receptacle 106 of the cover 104A is enclosed inside the tube 102A and holds the consumable substance 138 for the organism of interest T, and new generations T' of the organism, which can include, without limitation, the non-adult form of the organism such as eggs, larvae and/or pupae. Moreover, a sealing film 150 may be bonded to the seal receiving surface 120 of the cover 104A to close the inlet port 108 thereof. The culture containers 100A can be provided on the conveyor system 202 with the covers 104A on top of the tubes 102A.

In step 304, the clean culture containers 100B can be provided on the conveyor system 204. The clean culture containers 100B initially provided may be sterilized containers enclosing no cultured organism. Each culture container 100B can include the tube 102B, the cover 104B closing the opening 103 of the tube 102B, and the air-permeable plug 136 closing the opening 105 of the tube 102B. The receptacle 106 of the cover 104B is enclosed inside the tube 102B, and can hold the consumable substance 138 for the organism of interest T. No sealing film is bonded to the seal receiving surface 120 or 122 of the cover 104B. The culture containers 100B can be provided on the conveyor system 204 with the covers 104B on top of the tubes 102B.

In step 306, the anesthetization unit 206 can anesthetize the organism of interest T that is enclosed inside each culture container 100A. For example the anesthetization unit 206 can deliver an anesthetic substance (e.g., dioxide carbon) into each culture container 100A through the inlet port 108 provided on the cover 104A thereof. More specifically, the nozzle 262 of the anesthetization unit 206 can pierce the sealing film 150 on the cover 104A, and then deliver the anesthetic substance through the inlet port 108 into the interior of the culture container 100A. The anesthetization unit 206 may deliver the anesthetic substance into each culture container 100A at a location adjacent to the rotary platform 224, after the culture container 100A is conveyed into the pressurized chamber 284. As a result, a portion of the anesthetized organism T, in particular the adult form thereof, can drop on the air-permeable plug 136 by gravity action. Meanwhile, a portion of the organism T, including the new generations T' thereof, can remain in the receptacle 106 of the cover 104A.

In next step 308, while a portion of the anesthetized organism T remains inside the tube 102A, the exchanging unit 208 can interchange the covers 104A and 104B between two culture containers 100A and 100B so that the cover 104A is attached to the tube 102B and the cover 104B is attached to the tube 102A. A portion of the organism T, in particular the new generations T' thereof, can be thereby transferred to a new culture container comprised of the tube 102B and the cover 104A.

Step 308 may be performed while the two culture containers 100A and 100B are positioned with the two covers 104A and 104B respectively on top of the two tubes 102A and 102B. For example, with reference to FIGS. 7 and 13, the rotary platform 224 of the conveyor system 202 can rotate to convey one culture container 100A from the anesthetization unit 206 to the exchanging unit 208, and the rotary platform 244 of the conveyor system 204 can rotate to convey one culture container 100B to the exchanging unit 208. While the two tubes 102A and 102B remain generally stationary on the rotary platforms 224 and 244, the rotary part 266 and the two arms 268 of the exchanging unit 208 then can slide downward along the pivot axis R so that the two arms 268 can respectively grasp the covers 104A and 104B, slide upward to respectively separate the covers 104A and 104B from the tubes 102A and 102B, rotate about the pivot axis R to move and switch the two covers 104A and 104B with respect to the two tubes 102A and 102B, slide downward to respectively attach the cover 104A to the tube 102B and the cover 104B cover to the tube 102A, and eventually slide upward to release the covers 104A and 104B and clear the way for downstream travel of the tubes 102A and 102B for further processing. After processing at the exchanging unit 208, the culture container 100A carried by the conveyor system 202 becomes a culture container 100A' comprised of the tube 102A and the cover 104B attached to each other, and the culture container 100B carried by the conveyor system 204 becomes a culture container 100B' comprised of the tube 102B and the cover 104A attached to each other.

Figure 18:
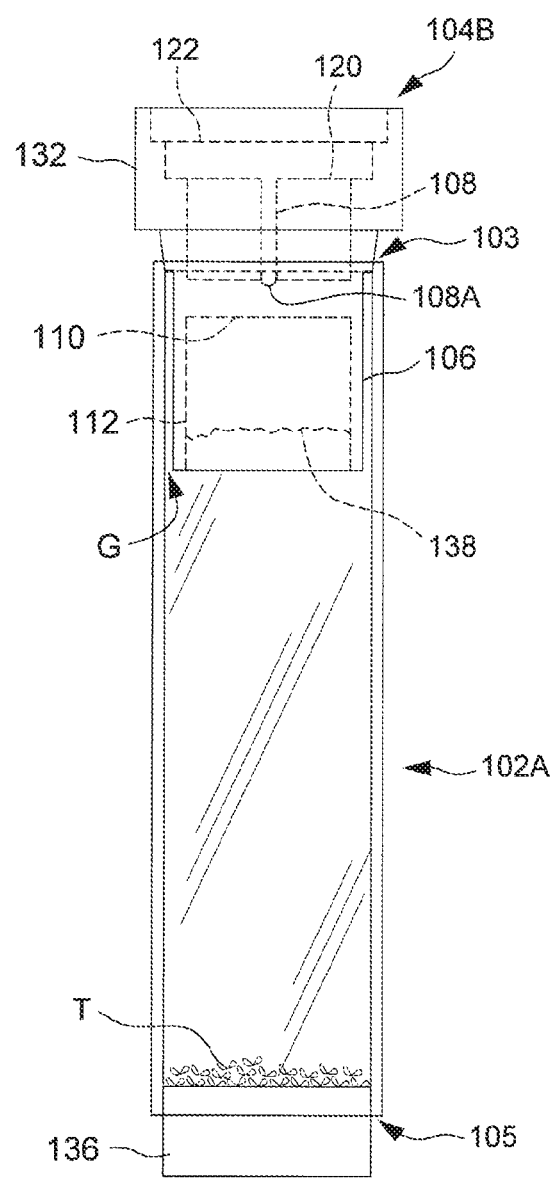
FIGS. 18 and 19 are two schematic views respectively illustrating the first and second culture containers after the respective covers thereof are interchanged.

FIG. 18 illustrates the culture container 100A'. In the culture container 100A', the organism of interest T (mostly the adult form thereof) can remain stunned on the air-permeable plug 136. The consumable substance 138 held in the receptacle 106 of the cover 104B can be used to continue culturing the organism of interest T inside the culture container 100A'.

Figure 19:
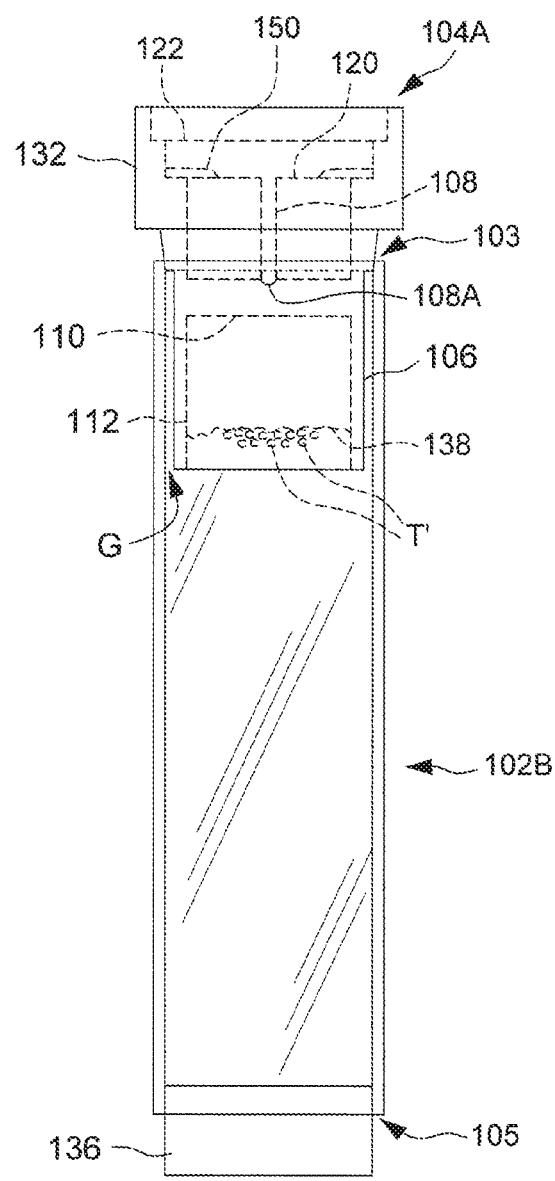

FIG. 19 illustrates the culture container 100B'. In the culture container 100B', the receptacle 106 of the cover 104A can hold the new generations T' of the organism of interest, which can include the non-adult form of the organism such as eggs, larvae and/or pupae. Moreover, the sealing film 150 on the cover 104A is shown as being broken, which is due to the introduction of the anesthetic substance into the culture container 100A at the anesthetization unit 206 when the cover 104A was attached to the tube 102A.

In step 310, the rotary platform 244 can convey the culture container 100B' downstream of the exchanging unit 208 to the reading unit 214, which can read an identification code on the cover 104A attached to the tube 102B.

Figure 21:
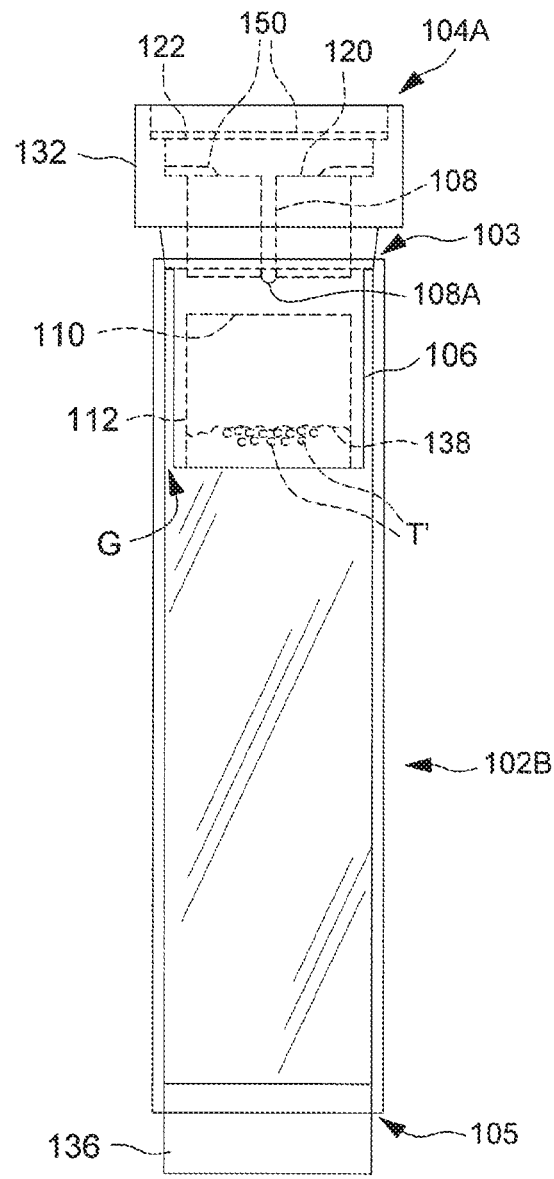
FIG. 21 is a schematic view illustrating the culture container of FIG. 19 having a sealing film bonded to the cover thereof.

In step 312, the rotary platform 244 can further convey the culture container 100B' to the sealing unit 212, which can bond a sealing film 150 on the seal receiving surface 122 of the cover 104A which is attached to the tube 102B (the other seal receiving surface 120 of the cover 104A already has another sealing film 150 bonded thereto). The culture container 100B' comprised of the cover 104A attached to the tube 102B and the sealing film 150 bonded to the seal receiving surface 122 of the cover 104A is illustrated in FIG. 21.

Figure 20:
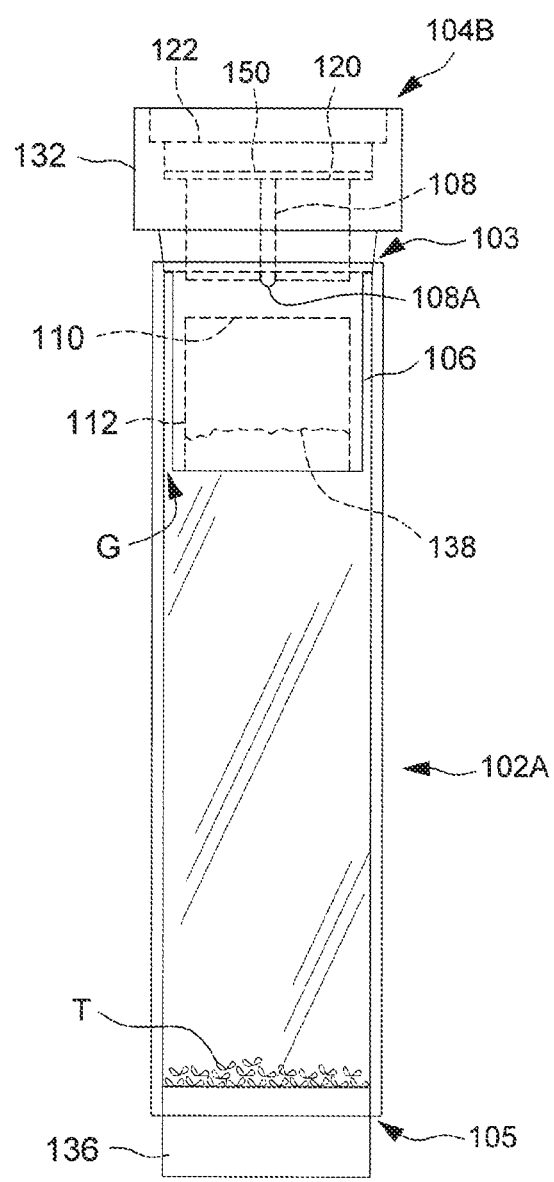
FIG. 20 is a schematic view illustrating the culture container of FIG. 18 having a sealing film bonded to the cover thereof.

In step 314, the rotary platform 224 can convey the culture container 100A' downstream of the exchanging unit 208 to the sealing unit 210, which can bond a sealing film 150 on the seal receiving surface 120 of the cover 104B which is attached to the tube 102A. The culture container 100A' comprised of the cover 104B attached to the tube 102A and the sealing film 150 bonded to the seal receiving surface 120 of the cover 104B is illustrated in FIG. 20.

In step 316, the rotary platform 224 can further convey the culture container 100A' to the printing unit 216, which can print an identification code on the cover 104B attached to the tube 102A according to the code read on the cover 104A in step 310. According to an example of implementation, the identification code printed on the cover 104B may be similar to that on the cover 104A. According to some embodiment, the identification code printed on the cover 104B may contain information such as a description of the organism of interest T, the date of transfer, and the like. In this manner, the cultured organism of interest T can be adequately identified and its chain of transfer may be suitably traced.

Figure 22:
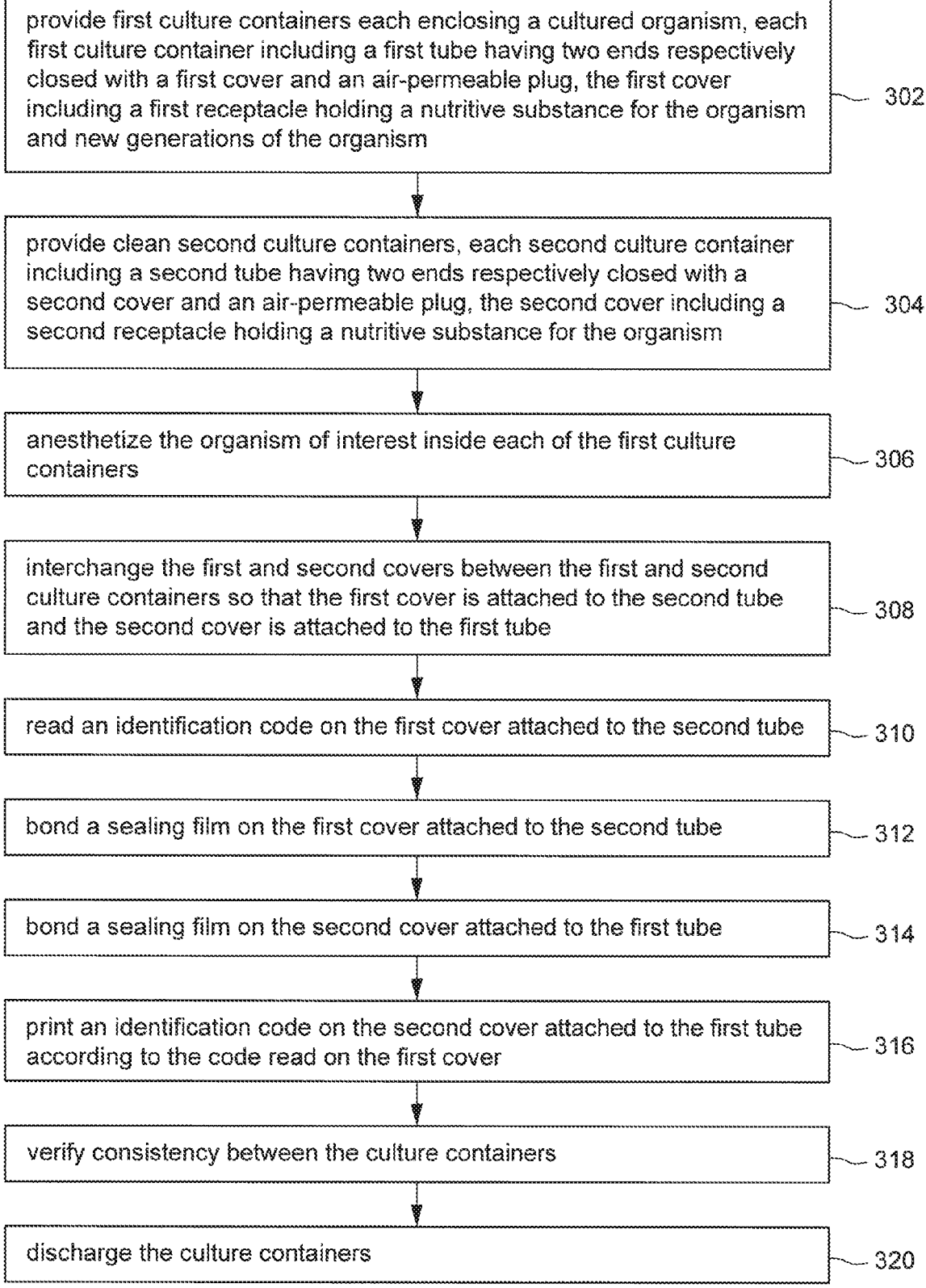
FIG. 22 is a flowchart of method steps executable on an automated transfer system.

While the flowchart of FIG. 22 exemplary illustrates steps 310, 312, 314 and 316 in a specific sequence, it will be appreciated that these steps may be performed in any suitable order. For example, some embodiment may perform step 310 before or after step 312 along the transport path P2. Some embodiment may perform step 314 before or after step 316 along the transport path P1. Some embodiment may perform step 314 and/or step 316 after or before step 312. Some embodiment may perform steps 312 and 314 before steps 310 and 316.

In step 318, before the culture containers 100A' and 100B' are respectively discharged to the receiving trays 240 and 258, the inspection units 218 and 220 can respectively read the identification codes on the covers 104B and 104A of the culture containers 100A' and 100B', and verify that they are consistent. In case they are not consistent, suitable correction steps may be taken. For example, the transfer system 200 may stop the transfer process, and issue an alert signal requesting further verification and/or correction. Alternatively, the default culture containers 100A' and/or 100B' may be automatically evacuated for further verification and/or correction.

After the culture containers 100A' and 100B' have passed the inspection units 218 and 220, the conveyor systems 202 and 204 in step 320 can respectively convey the culture containers 100A' and 100B' out of the pressurized chamber 284 and respectively discharge them on the receiving trays 240 and 258. New generations T' of the organism of interest T can be thereby grown and maintained in the culture containers 100B', whereas the culture containers 100A' can be kept as backup stocks. The culture containers 100A' and 100B' may be turned over so that the cover 104 of each culture container 100A' and 100B' is at the bottom for culturing the organism of interest T.

Figure 23:
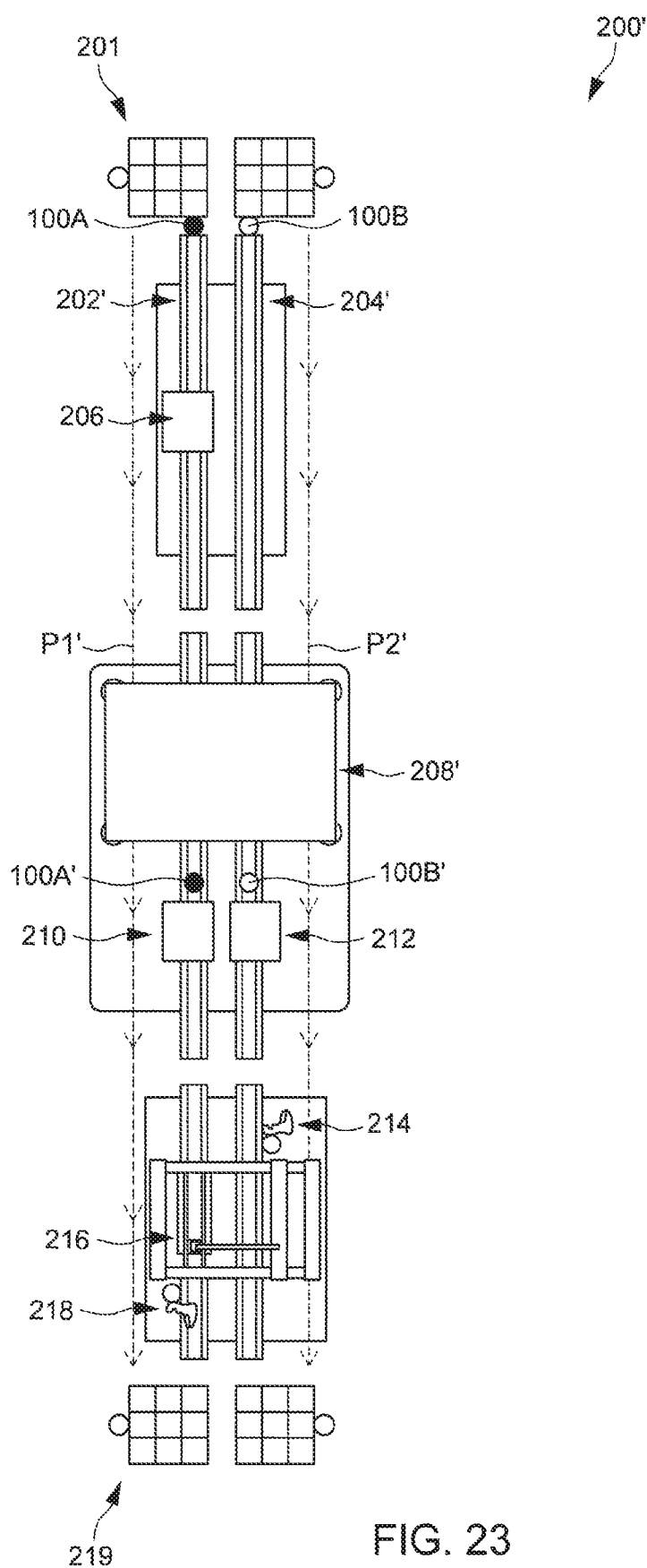
FIG. 23 is a schematic planar view illustrating a variant construction of an automated transfer system operable to transfer a cultured organism of interest between a plurality of culture containers.

FIG. 23 is a schematic planar view illustrating a variant construction of an automated transfer system 200' that can transfer a cultured organism of interest between the culture containers 100A and 100B. Like previously described, the transfer system 200' can include two conveyor systems 202' and 204', the anesthetization unit 206, an exchanging unit 208', the two sealing units 210 and 212, the reading unit 214, the printing unit 216 and the inspection unit 218.

Like in the previous embodiment, the conveyor system 202' can define a transport path P1' along which the culture containers 100A may be conveyed in a row for processing, and the conveyor system 204' can define a transport path P2' along which the culture containers 100B may be conveyed in a row for processing. The two transport paths P1' and P2' can be substantially linear and parallel to each other, and each of the conveyor systems 202' and 204' can include one or more conveyor belt. The two conveyor systems 202' and 204' can respectively carry the culture containers 100A and 100B with the covers 104A and 104B respectively on top of the tubes 102A and 102B.

In order to position the culture containers 100A and 100B in the suitable orientation for processing, the transfer system 200' may further include a flipping unit 201 disposed upstream of the conveyor systems 202' and 204'. The flipping unit 201 can have a space that can receive a larger quantity of culture containers 100A and 100B. The flipping unit 201 can rotate 180 degrees the culture containers 100A and 100B so that the covers 104A and 104B are respectively on top of the tubes 102A and 102B.

Like previously described, the anesthetization unit 206 may be disposed adjacent to the conveyor system 202', and upstream of the exchanging unit 208'. The anesthetization unit 206 is operable to deliver an anesthetic substance into each culture container 100A through the inlet port 108 (better shown in FIG. 16) provided on the cover 104A for anesthetizing the organism of interest enclosed in the culture container 100A. The anesthetization unit 206 may have a construction similar to that illustrated in FIG. 12.

The exchanging unit 208' is disposed downstream of the anesthetization unit 206 along the transport path P1'. The exchanging unit 208' can be positioned between the two conveyor systems 202' and 204', which can respectively carry the culture containers 100A and 100B toward the exchanging unit 208' with the covers 104A and 104B respectively on top of the tubes 102A and 102B. Like previously described, the exchanging unit 208 is operable to interchange the covers 104A and 104B between two culture containers 100A and 100B, so that the cover 104A initially attached to the tube 102A of the culture container 100A becomes attached to the tube 102B of the initially provided culture container 100B, and the cover 104B initially attached to the tube 102B of the culture container 100B becomes attached to the tube 102A of the initially provided culture container 100A.

Figure 24:
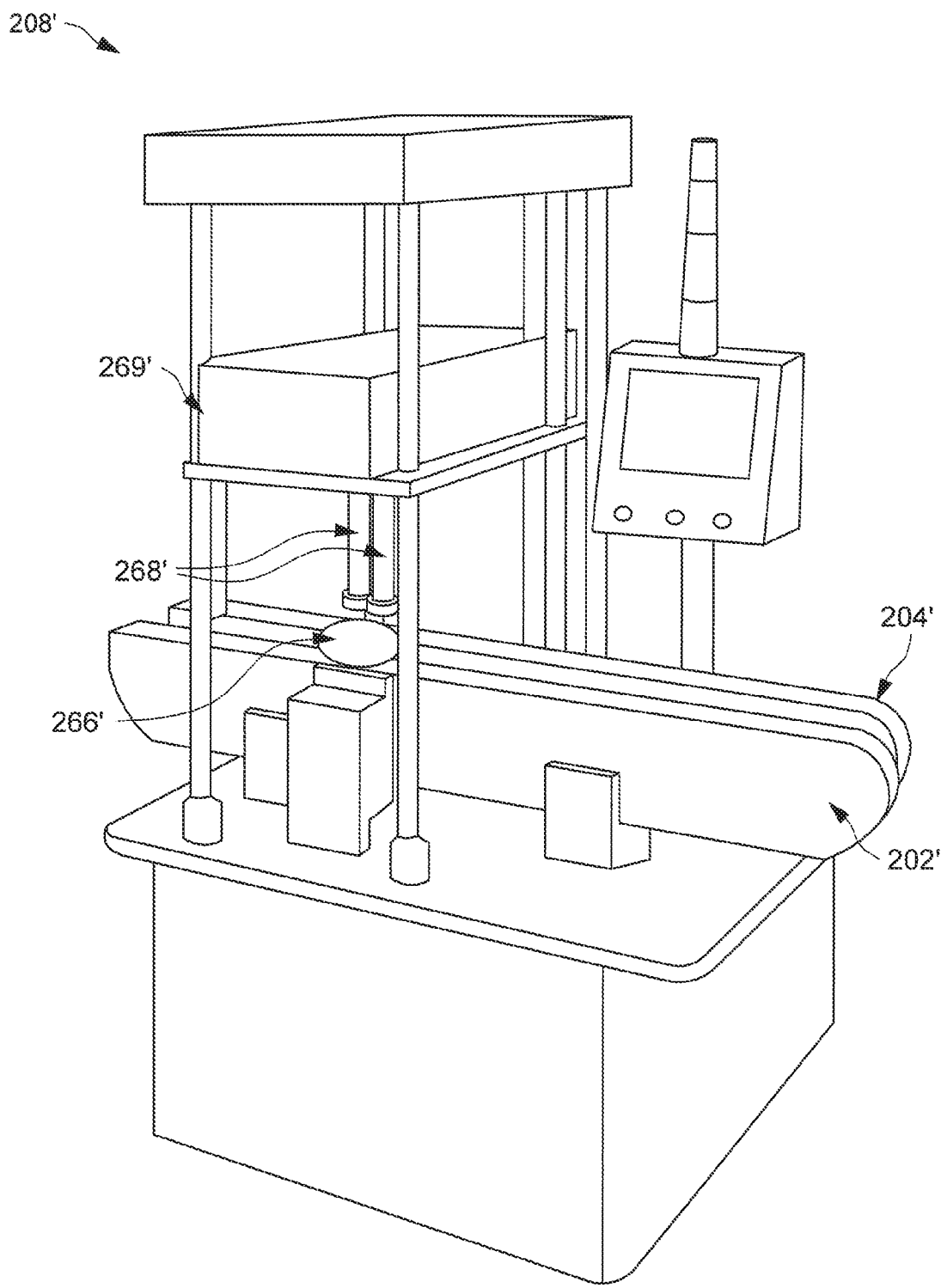
FIG. 24 is a schematic view illustrating a construction of an exchanging unit provided in the transfer system shown in FIG. 23.

In conjunction with FIG. 23, FIG. 24 is a schematic view illustrating a construction of the exchanging unit 208'. Referring to FIGS. 23 and 24, the exchanging unit 208' can include a rotary part 266', and two arms 268' extending above the rotary part 266'. The rotary part 266' may be a rotary disk. The conveyor systems 202' and 204' can respectively transport the culture containers 100A and 100B until they are positioned on the rotary part 266', which can provide support for the tubes 102A and 102B of the culture containers 100A and 100B at an underside thereof. The two arms 268' are movable vertically, and can be configured to respectively hold the two covers 104A and 104B at the catch portions 132 thereof. Each of the two arms 268' is operable to separate or attach one cover 104A or 104B with respect to one tube 102A or 102B, and the rotary part 266' is rotatable to move the two tubes 102A and 102B while the two covers 104A and 104B are kept stationary by the two arms 268'. The exchanging unit 208' can thereby switch the two covers 104A and 104B with respect to the two tubes 102A and 102B.

According to some embodiment, the exchanging unit 208' may further include an air curtain 269' operable to prevent air or contaminants from moving into a space where the culture containers 100A and 100B are positioned for switching the two covers 104A and 104B with respect to the two tubes 102A and 102B. This may prevent contamination of the culture container 100A' comprised of the cover 104B attached to the tube 102A and the culture container 100B' comprised of the cover 104A attached to the tube 102B.

Referring again to FIG. 23, the two sealing units 210 and 212 may be respectively disposed adjacent to the conveyor systems 202' and 204' downstream of the exchanging unit 208' along the transport paths P1' and P2'. Like previously described, the sealing unit 210 can bond a sealing film on the cover 104B attached to the tube 102A, and the sealing unit 212 can bond another sealing film on the cover 104A attached to the tube 102B.

The reading unit 214 can be disposed adjacent to the transport path P2' downstream of the exchanging unit 208', e.g., downstream (as shown) or upstream of the sealing unit 212 along the transport path P2'. The reading unit 214 can read an identification code on the cover 104A attached to the tube 102B of the culture container 100B'.

The printing unit 216 can be disposed adjacent to the transport path P1' downstream of the exchanging unit 208', e.g., downstream (as shown) or upstream of the sealing unit 210 along the transport path P1'. The printing unit 216 can print an identification code on the cover 104B attached to the tube 102A of the culture container 100A' according to the identification code read on the cover 104A by the reading unit 214. The inspection unit 218 can be disposed downstream of the printing unit 216 along the transport path P1', and can verify whether the identification code printed on the cover 104B by the printing unit 216 is correct.

Referring to FIG. 23, the transfer system 200' may further include a flipping unit 219 disposed adjacent to an end of each of the conveyor system 202' and 204' opposite to the flipping unit 201. The flipping unit 219 can rotate 180 degrees the culture containers 100A' and 100B' so that the covers 104B and 104A are respectively at the bottom of the tubes 102A and 102B.

Like the transfer system 200 described previously, the transfer system 200' can be adapted to perform the method steps illustrated in the flowchart of FIG. 22 for transferring the organism of interest between the culture containers.

Advantages of the culture containers, systems and method described herein include the ability to culture and transfer large stocks of an organism of interest in an efficient manner. Rather than transferring the organism itself, the systems and method described herein transfer a cover of the culture container that can hold new generations of the organism of interest, which can greatly facilitate the transfer operation.

Realizations of the structures and methods have been described only in the context of particular embodiments. These embodiments are meant to be illustrative and not limiting. Many variations, modifications, additions, and improvements are possible. Accordingly, plural instances may be provided for components described herein as a single instance. Structures and functionality presented as discrete components in the exemplary configurations may be implemented as a combined structure or component. These and other variations, modifications, additions, and improvements may fall within the scope of the claims that follow.

What is claimed is:

1. A transfer system comprising:
   a first conveyor system for transporting at least a first culture container along a first path, wherein the first culture container includes a first tube having two openings at two opposite ends thereof and a removable first cover attached to one of the two openings of the first tube, the first cover including a first receptacle for holding a substance consumable by an organism of interest, the first receptacle being enclosed inside the first tube when the first cover is attached to the first tube;
   a second conveyor system for transporting at least a second culture container along a second path, wherein the second culture container includes a second tube having two openings at two opposite ends thereof and a removable second cover attached to one of the two openings of the second tube, the second cover including a second receptacle for holding a substance consumable by an organism of interest, the second receptacle being enclosed inside the second tube when the second cover is attached to the second tube; and
   an exchanging unit disposed between the first and second conveyor systems, the exchanging unit being operable to interchange the first and second covers between the first and second culture containers so that the first cover is attached to the second tube and the second cover is attached to the first tube.

2. The transfer system according to claim 1, wherein the exchanging unit is operable to:
   respectively separate the first and second covers from the first and second tubes;
   switch the first and second covers with respect to the first and second tubes; and
   respectively attach the first cover to the second tube and the second cover to the first tube.

3. The transfer system according to claim 2, wherein the exchanging unit switches the first and second covers with respect to the first and second tubes by moving the first and second covers while keeping the first and second tubes stationary, or by moving the first and second tubes while keeping the first and second covers stationary.

4. The transfer system according to claim 2, wherein the exchanging unit includes a rotary part operable to switch the first and second covers with respect to the first and second tubes.

5. The transfer system according to claim 4, wherein the exchanging unit further includes two arms that are connected with the rotary part at two diametrically opposite positions relative to a pivot axis of the rotary part, each of the two arms being operable to separate or attach one cover with respect to one tube, the rotary part and the two arms being rotatable to move the first and second covers while the first and second tubes remain stationary.

6. The transfer system according to claim 5, wherein each of the two arms is configured to hold one cover at a catch portion provided on the cover.

7. The transfer system according to claim 4, wherein the exchanging unit further includes two arms extending above the rotary part, each of the two arms being operable to separate or attach one cover with respect to one tube, and the rotary part being rotatable to move the first and second tubes while the first and second covers are kept stationary by the two arms.

8. The transfer system according to claim 1, further comprising an anesthetization unit disposed adjacent to the first conveyor system and upstream of the exchanging unit, the anesthetization unit being operable to anesthetize an organism of interest enclosed inside the first culture container.

9. The transfer system according to claim 8, wherein the anesthetization unit is operable to deliver an anesthetic substance into the first culture container through the first cover thereof for anesthetizing an organism of interest enclosed inside the first culture container.

10. The transfer system according to claim 9, wherein the first cover attached to the first tube has a sealing film for preventing fluid passage through the first inlet port into the hollow interior of the first tube, and the anesthetization unit is further operable to pierce the sealing film before delivering the anesthetic substance into the first culture container.

11. The transfer system according to claim 1, further comprising a first sealing unit operable to bond a first sealing film on the second cover attached to the first tube, and a second sealing unit operable to bond a second sealing film on the first cover attached to the second tube.

12. The transfer system according to claim 1, further comprising a reading unit disposed adjacent to the second path, and a printing unit disposed adjacent to the first path, the reading unit being operable to read a code on the first cover attached to the second tube, and the printing unit being operable to print an identification code on the second cover attached to the first tube according to the code read on the first cover.

13. The transfer system according to claim 1, wherein the first conveyor system includes a rotary platform, a container supplying part for delivering the first culture container comprised of the first tube and the first cover to the rotary platform, and a container discharging part, the rotary platform including at least one slot for receiving the first tube, the rotary platform being operable to convey the first tube received in the slot from the container supplying part through the exchanging unit to the container discharging part.

14. The transfer system according to claim 13, wherein any of the container supplying part and the container discharging part includes a ramp or a conveying belt.

15. The transfer system according to claim 1, wherein the second conveyor system includes a second rotary platform, a second container supplying part for delivering the second culture container comprised of the second tube and the second cover to the second rotary platform, and a second container discharging part, the second rotary platform including at least one second slot for receiving the second tube, the second rotary platform being operable to convey the second tube received in the second slot from the second container supplying part through the exchanging unit to the second container discharging part.

16. The transfer system according to claim 1, wherein the first and second conveyor systems are operable to respectively carry the first and second culture containers toward the exchanging unit with the first and second covers respectively on top of the first and second tubes.

17. The transfer system according to claim 1, further comprising a pressurized chamber, the exchanging unit being disposed inside the pressurized chamber, and the first and second conveyor systems are respectively operable to convey the first and second culture containers into the pressurized chamber.

* * * * *